(12) United States Patent
Launay et al.

(10) Patent No.: US 6,710,064 B2
(45) Date of Patent: Mar. 23, 2004

(54) HYDANTOIN COMPOUNDS USEFUL AS ANTI-INFLAMMATORY AGENTS

(75) Inventors: Michele Launay, Rueil Malmaison (FR); Dominique Potin, Aubergenville (FR); Magali Jeannine Blandine Maillet, Courbevoie (FR); Eric Antoine Nicolai, Rueil Malmaison (FR); T. G. Murali Dhar, Newtown, PA (US); Edwin J. Iwanowicz, Cranbury, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 11 days.

(21) Appl. No.: 10/000,389

(22) Filed: Nov. 30, 2001

(65) Prior Publication Data

US 2002/0143035 A1 Oct. 3, 2002

Related U.S. Application Data

(60) Provisional application No. 60/250,486, filed on Dec. 1, 2000, provisional application No. 60/250,653, filed on Dec. 1, 2000, and provisional application No. 60/272,165, filed on Feb. 28, 2001.

(51) Int. Cl.$^7$ .................... A61K 31/4184; C07D 235/02
(52) U.S. Cl. .................. 514/387; 548/302.4; 548/302.7
(58) Field of Search ....................... 514/387; 548/302.4, 548/302.7

(56) References Cited

U.S. PATENT DOCUMENTS

| 5,482,921 A | 1/1996 | Seckinger et al. |
| 5,605,877 A | 2/1997 | Schafer et al. |

FOREIGN PATENT DOCUMENTS

| AU | A-82875/87 | 6/1988 |
| DE | 2354086 | 5/1974 |
| EP | 0272594 | 6/1988 |
| EP | 1004583 | 5/2000 |
| JP | 5540653 | 3/1980 |
| WO | WO94/05668 | 3/1994 |
| WO | WO98/08813 | 3/1998 |
| WO | WO98/39303 | 9/1998 |
| WO | WO00/13508 | 6/2000 |
| WO | WO01/07052 | 2/2001 |
| WO | WO01/30781 | 5/2001 |
| WO | WO02/08227 A2 | 1/2002 |

OTHER PUBLICATIONS

Issartel et al.; Eur. J. Med. Chem., 31, pp. 717–723 (1996).
Winstead et al.; J. of Med. Chem. p. 142 (1966).
Nam et al.; Arch. Pharm. Pharm. Med. Chem. pp. 268–270 (1997).
Corey et al.; J. of the Am. Chemical Society, 92:8, pp. 2476–2480 (1970).
Abstract, XP–002196369, ComGenex Product List, Am. Chem. Soc.; 1999.
Abstract, XP–002196370, ComGenex Product List, Am. Chem. Soc.; 1999.
Abstract, XP–002196371, ComGenex Product List, Am. Chem. Soc.; 1999.
Abstract, XP–002196372, ComGenex Product List, Am. Chem. Soc.; 1999.
Abstract, XP–002196373, ComGenex Product List, Am. Chem. Soc.; 1999.
Abstract, XP–002196374, ComGenex Product List, Am. Chem. Soc.; 1999.
Abstract, XP–002196375, ComGenex Product List, Am. Chem. Soc.; 1999.
Abstract, XP–002196376, ComGenex Product List, Am. Chem. Soc.; 1999.
Abstract, XP–002196377, ComGenex Product List, Am. Chem. Soc.; 1999.
Abstract, XP–002196368, Chem. Abstracts Service, Vol 101, No. 110818, 1984.
Migawa et al. Organic Letters, vol. 2, No. 21, pp. 3309–3311, 2000.
Deprez et al., Tetrahedron: Asymmetry, Vol 2, No. 12, pp. 1189–1192, 1991.
Wittland, et al. Synthesis (11), pp. 1291–1295, 1997.
Deprez et al., Tetrahedron vol. 49, No. 18, pp. 3781–3792, 1993.

*Primary Examiner*—Deborah C. Lambkin
*Assistant Examiner*—Sonya Wright
(74) *Attorney, Agent, or Firm*—Anastasia P. Winslow; Lauralee A. Duncan

(57) ABSTRACT

Compounds having the formula (I):

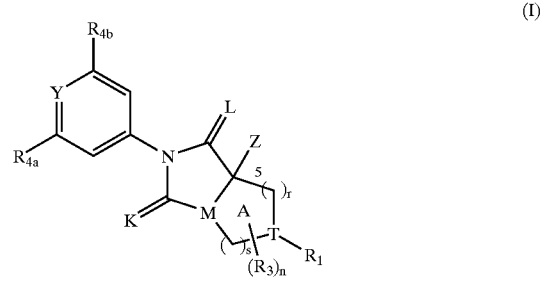

and pharmaceutically-acceptable salts thereof, are useful for treating inflammatory or immune diseases, in which A is a four to seven membered heterocyclic or carbocyclic saturated ring; L and K are O or S; M is N or CH; Y is N or CH; Z is hydrogen, alkyl or substituted alkyl; and $R_1$–$R_4$ are as defined in the specification.

19 Claims, No Drawings

HYDANTOIN COMPOUNDS USEFUL AS ANTI-INFLAMMATORY AGENTS

RELATED INVENTIONS

This application claims the benefit of U.S. application Ser. Nos. 60/250,486 and 60/250,653, both filed Dec. 1, 2000, and U.S. application Ser. No. 60/272,165, filed Feb. 28, 2001, the contents of which are incorporated herein by reference.

FIELD OF THE INVENTION

The present invention relates to hydantoin compounds, pharmaceutical compositions containing them, and methods of using such compounds in treating inflammatory or immune disease.

BACKGROUND OF THE INVENTION

Cells adhere to other cells and to substrates through specific, regulated processes that are critical to various biological functions. The proper functioning of the immune system, for example, is dependent upon adhesive interactions and cell migration. A key event in an immune response involves the migration of leukocytes to a disease site. During an inflammatory response, leukocytes are recruited to the site of injury and extravasated by a series of cellular interactions involving cell-cell and cell-substrate adhesion.

One family of molecules that serve an important adhesive function are integrins. Integrins are expressed on cell surfaces and function in cell-cell and cell-substrate adhesion. Integrins are alpha-beta heterodimers: each integrin has an alpha ($\alpha$) subunit non-covalently binded to a beta ($\beta$) subunit. When activated, integrins bind to extracellular ligands and induce adhesion (the expression of integrins on a cell surface alone is inadequate for adhesion—they must be activated to become adhesive). The integrin activation state is transient, such that there is a rapid flux between adhesive and non-adhesive states which is important for cell movement, e.g., a cell is endowed with the ability to rapidly adhere to various cell surfaces and matrices and to migrate among cells and tissue.

There are four known integrins having a $\beta_2$ or CD18 subunit which comprise the CD11/CD18 integrin subfamily, namely, Lymphocyte Function-associated Antigen 1 (LFA-1) (CD11a/CD18 or $\alpha_L\beta_2$); Macrophage Antigen 1 (Mac-1) (CD11b/CD18 or $\alpha_M\beta_2$); p150,95 (CD11c/CD18 or $\alpha_X\beta_2$); and $\alpha_D\beta_2$. The CD11/CD18 family of integrins are also referred to as Leukointegrins as they are expressed on the surface of various leukocyte cells, and they mediate a number of inflammation-related cellular interactions. See Diamond et al., "The Dynamic Regulation of Integrin Adhesiveness," Current Biology, Vol. 4 (1994) at pp. 506–532.

Ligands to LFA-1 and Mac-1 comprise the intercellular adhesion molecule (ICAM) ICAM-1. LFA-1, the primary CD11/CD18 integrin, also binds with ICAM-2 and ICAM-3. ICAMs are found on endothelium cells, leukocytes, and other cell types, and their interaction with CD11/CD18 integrins is critical to immune system function. The interaction between the CD18 integrins, particularly LFA-1, and ICAMs mediates antigen presentation, T-cell proliferation, and adhesion between the endothelium and activated leukocytes which is necessary for leukocytes to migrate from the circulatory system into tissue. A condition termed "Leukocyte Adhesion Deficiency" has been identified in patients having a severe deficiency in CD18 integrins. These patients are unable to mount a normal inflammatory or immune response; they suffer from disorders such as recurrent infections, poor wound healing, granulocytosis, progressive periodontitis, and umbilical cord separation. See Anderson et al., "Leukocyte LFA-1, OKMI, p150,95 Deficiency Syndrome: Functional and Biosynthesis Studies of Three Kindreds," Fed. Proc., Vol. 44 (1985), pp. 2671–2677.

While sufficient levels of CD18 integrins interacting with ICAMs are needed to mount a normal immune response, significant cellular and tissue injury can result in chronic inflammatory states where there is an inappropriate influx of leukocytes to the disease site. Continuous recruitment of leukocytes from blood vessels into inflamed tissue, as in chronic inflammatory states, can perpetuate tissue injury and lead to excessive fibrous repair and autoimmune disease. Thus, inhibition of the interaction between LFA-1 and/or Mac-1 and their ICAMs can be advantageous in treating inflammatory or immune disease. For example, monoclonal antibody blockade of either ICAM or LFA-1 has been shown to prevent the migration of leukocytes into tissue and the subsequent development of inflammatory disease in animal models of rheumatoid arthritis, inflammatory bowel disease, and pulmonary inflammation (e.g., asthma). Knockout mice deficient in ICAMs have reduced susceptibility to induced arthritis, ischemia injury, impaired lung inflammatory responses, and increased tolerance to transplantations (e.g. heart grafts). See Anderson, supra. Antibodies blocking the ICAM-LFA-1 interaction reportedly suppress cardiac allograft rejection and islet cell xenograft rejection in animal models. See Gorski, "The Role of Cell Adhesion Molecules in Immunopathology," Immunology Today, Vol. 15 (1994), at pp. 251–255.

Compounds inhibiting CD18 integrins, ICAMs, or the LFA-1:ICAM interaction could potentially demonstrate a wide range of utilities in treating inflammatory or immune diseases. Blocking LFA-1 reportedly inhibits the influx of leukocytes in almost every system, including the skin, peritoneum, synovium, lung, kidney and heart, and blocking ICAM-1 would be expected to have similar effects. Also, present therapies for many inflammatory or immune diseases have drawbacks. For example, current treatments for asthma include $\beta_2$-agonists, inhaled corticosteroids, and $LTD_4$ antagonists. However, $\beta_2$-agonists have limited efficacy and inhaled corticosteroids raise safety concerns. To treat psoriasis, current therapies include PUVA, methotrexate, cyclosporin A, and topical treatments. The first three of those therapies raise toxicity issues over long-term (6–9 month) use, whereas topical treatments have limited efficacy. Additionally, these treatments typically are applied only in response to flares and not as a prophylaxis measure. There is a need for pharmaceuticals having increased effectiveness and fewer side effects.

Accordingly, there is interest in developing Leukointegrin or ICAM antibodies and antagonists of Leukointegrins and/or ICAMs. Thiadiazole-based compounds reportedly inhibit LFA-1 and Mac-1 binding with ICAM-1 and are claimed to be useful as anti-inflammatory agents. See Intern. Pub. No. WO 99/20,618, "Thiadiazole Amides Useful as Anti-Inflammatory Agents" filed by Pharmacia & Upjohn Co. (See also WO 99/20,617, also to Pharmacia and Upjohn.) Thiazole compounds linked to phenyl and pyrazole rings are claimed to be active LFA-1/ICAM inhibitors. Sanfilippo et al., "Novel Thiazole Based Heterocycles as Inhibitors of LFA-1/ICAM-1 Mediated Cell Adhesion," J. Med. Chem. Vol. 38 (1995) at pp.1057–1059. A series of small molecules comprising 1-(3,5 dichlorophenyl) imidazolidines are claimed to be antagonists to the binding of ICAMs with CD18 integrins. See Intern. Pub. No. WO 98/39303, "*Small Molecules Useful in the Treatment of Inflammatory Disease*," filed by Boehringer Ingelheim Pharmaceuticals, Inc. (See also Boehringer patent applications WO 01/07052, WO 01/07048, WO 01/07044, WO 01/06984, and WO 01/07440). A series of compounds comprising various benzylamines and 2-bromobenzoyl-tryptophan are claimed to be antagonists to LFA-1/ICAM-1 receptor binding. See Intern. Pub. No. WO99/49,856, "*Antagonists for Treatment of CD11/CD18 Adhesion Receptor Mediated Disorders*," filed by Genentech, Inc. See also Intern. Pub. No. WO 00/21,920, "*Diaminopropionic Acid Derivatives*," filed by Hoffmann-La Roche Inc., disclosing a series of compounds claimed to block ICAM activity and have particular utility in treating reperfusion injury following acute myocardial infarction.

As may be appreciated, those in the field of pharmaceutical research continue to seek to develop new compounds and compositions for treating inflammatory or immune disease such as inhibitors of Leukointegrins and/or ICAMs. Particularly in the area of immune response, many individuals respond differently to different drugs. Thus, there is an interest in providing consumers not only with pharmaceutical compounds and compositions demonstrating increased effectiveness and reduced side-effects but also different structures or mechanisms of action to provide consumers with a choice of options. The instant invention is directed to hydantoin compounds that are effective as antagonists of Leukointegrins and/or ICAMs. Hydantoin compounds are disclosed in European patent application Serial No. 0 272 594 A2 to Hoechst Aktiengesellschaft for use as herbicides; in U.S. Pat. No. 5,605,877 to Schafer et al. for use as herbicides; and in European patent application Ser. No. EP 1 004 583 A2 and Intern. Pub. No. WO 98/58,947 both to Pfizer Inc., for use as intermediates in making growth hormone secretagogues. Hydantoin compounds are disclosed in Intern. Pub. No. WO 01/30781 A2 (published May 3, 2001) to Tanabe Seiyaku Co. Ltd, "*Inhibitors of $\alpha_L\beta_2$ Mediated Cell Adhesion.*"

Each of the patents, patent applications and publications referenced above and hereinafter is incorporated herein by reference.

SUMMARY OF THE INVENTION

The present invention provides compounds useful for treating inflammatory or immune disease having the formula (I):

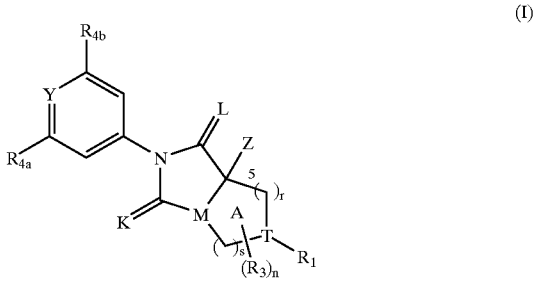

(I)

and pharmaceutically-acceptable salts thereof, in which:

L and K, taken independently, are O or S;
M is N or CH;
Y is CH or N;
Z is hydrogen, alkyl, or substituted alkyl, provided that Z may be selected from arylalkyl and heteroarylalkyl only when M is CH and/or when ring A has a second ring fused thereto;
T is nitrogen, CH, or a carbon atom substituted with an $R_3$ group;
$R_1$ is Q-aryl or Q-heteroaryl, wherein (a) when T is not nitrogen, Q is selected from a bond, —O—, —$NR_{10}$—, —S—, —C(=O)—, —$CO_2$—, —OC(=O)—, —$NR_{10}$C(=O)—, —C(=O)$NR_{10}$—, —$NR_{10}CO_2$—, $C_{1-4}$alkylene, $C_{1-4}$substituted alkylene, $C_{1-4}$alkenylene, $C_{1-4}$substituted alkenylene, and optionally-substituted bivalent $C_{1-4}$alkoxy, $C_{1-4}$alkylthio, $C_{1-4}$alkylamino, $C_{1-4}$aminoalkyl, $C_{0-4}$alkylsulfonyl, $C_{0-4}$alkylsulfonamide, $C_{1-4}$acyl, or $C_{0-4}$alkoxycarbonyl, or when Z is arylalkyl or heteroarylalkyl, $R_1$ may join with an $R_3$ group to form a fused carbocyclic or heterocyclic ring; or (b) when T is nitrogen, then Q is selected from a bond, —C(=O)—, —$CO_2$—, —OC(=O)—, —$C_{1-4}$alkylene, $C_{1-4}$substituted alkylene, $C_{1-4}$alkenylene, $C_{1-4}$substituted alkenylene, or optionally-substituted bivalent $C_{1-4}$alkoxy, $C_{1-4}$alkylthio, $C_{1-4}$aminoalkyl, $C_{0-4}$alkylsulfonyl, $C_{0-4}$alkylsulfonamide, $C_{1-4}$acyl, or $C_{1-4}$alkoxycarbonyl, provided that when M is N, T is N, r is 1, and s is 2 such that ring A is piperazine, $R_1$ is not an amine-protecting group;

$R_3$ is selected from at least one of (i) a substituent $R_3$, wherein each substituent $R_3$ is individually attached to any available carbon or nitrogen atom of ring A and at each occurrence is selected independently of each other $R_3$ from halogen, alkyl, substituted alkyl, alkenyl, alkynyl, nitro, cyano, $OR_8$, $NR_8R_9$, $CO_2R_8$, (C=O)$R_8$, C(=O)$NR_8R_9$, $NR_8C$(=O)$R_9$, $NR_8C$(=O)$OR_9$, OC(=O)$R_8$, OC(=O)$NR_8R_9$, $SR_8$, $S(O)_qR_{8a}$, $NR_8SO_2R_9$, $SO_2NR_8R_9$, aryl, heteroaryl, heterocyclo, and cycloalkyl, and when attached to an atom of ring A other than T, $R_3$ is optionally keto (=O), provided that when $R_3$ is attached to the atom designated as the C-5 atom of ring A, then $R_3$ is not aryl or heteroaryl; and (ii) a first group $R_3$ and a second group $R_3$, wherein the first group $R_3$ and the second group $R_3$ are attached to two adjacent atoms of ring A and together form an optionally-substituted carbocyclic or heterocyclic ring fused to ring A;

$R_{4a}$ and $R_{4b}$ are selected independently of each other from the group consisting of hydrogen, halogen, alkyl, substituted alkyl, alkenyl, alkynyl, nitro, cyano, hydroxy, alkoxy, substituted alkoxy, phenyloxy, benzyloxy, $CO_2H$, C(=O)H, amino, alkylamino, substituted alkylamino, $CO_2$alkyl, (C=O)alkyl, and alkylthio;

$R_8$ and $R_9$ (i) selected independently of each other are hydrogen, alkyl, substituted alkyl, alkenyl, alkynyl, alkoxy, cycloalkyl, aryl, heteroaryl, or heterocyclo; or (ii) taken together form a heterocyclo ring;

$R_{8a}$ is alkyl, substituted alkyl, cycloalkyl, aryl, heteroaryl, or heterocyclo;

$R_{10}$ is hydrogen, alkyl, or substituted alkyl;
n is 0, 1, or 2;
q is 1, 2, or 3;
r is 1 or 2; and
s is 0, 1, or 2.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth.

The term "substituted alkyl" refers to an alkyl group as defined above having one, two, or three substituents selected from the group consisting of halo, alkenyl, alkynyl, nitro, cyano, amino, hydroxy, alkoxy, alkylthio, —$NHSO_2$, —N(alkyl)$SO_2$, —$NHSO_2$(alkyl), —$NHSO_2$(aryl), —N(alkyl)$SO_2$(alkyl), —N(alkyl)$SO_2$(aryl), —$SO_2$(alkyl), —$SO_2$(aryl), —$SO_2$N(aryl)(alkyl), —$SO_2$N(alkyl)$_2$, —NH (alkyl), —NH(cycloalkyl), —N(alkyl)$_2$, —CO$_2$H, —C(=O)H, —CO$_2$-alkyl, —(C=O)alkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, keto (=O), =N—OH, =N—O-alkyl, aryl, heteroaryl, heterocyclo, and cycloalkyl, including phenyl, benzyl, phenylethyl, phenyloxy, and phenylthio. When a substituted alkyl includes an aryl, heterocyclo, heteroaryl, or cycloalkyl substituent, said ringed systems are as defined below and thus may have zero, one, two, or three substituents, also as defined below.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above.

The term "alkoxy" refers to an alkyl group as defined above having a carbon atom replaced by one or more oxygen atoms. For example, the term "alkoxy" includes the groups —O—C$_{1-12}$alkyl, —C$_{1-6}$alkylene-O—C$_{1-6}$alkyl, and so forth.

The term "alkylthio" refers to an alkyl group as defined above having a carbon atom replaced by one or more sulfur (—S—) atoms. For example, the term "alkylthio" includes the groups —S—C$_{1-12}$alkyl, —C$_{1-6}$alkylene-S—C$_{1-6}$alkyl, etc.

The term "alkylamino" refers to an alkyl group as defined above bonded through one or more nitrogen atoms (e.g., —NR— groups). For example, the term "alkylamino" includes the groups —NH—C$_{1-12}$alkyl, —NH—C$_{1-6}$alkylene-NH—C$_{1-6}$alkyl, etc. The term alkylamino refers to straight and branched chain groups and thus, for example, includes the groups —NH(C$_{1-12}$alkyl) and —N(C$_{1-6}$alkyl)$_2$. When a subscript is used with reference to an alkoxy, alkylthio or alkylamino, the subscript refers to the number of carbon atoms that the group may contain in addition to heteroatoms. Thus, for example, monovalent C$_{1-2}$alkylamino includes the groups —NH—CH$_3$, —NH—CH$_2$—CH$_3$, and —N—(CH$_3$)$_2$.

When reference is made to a substituted alkoxy, substituted alkylthio, or substituted alkylamino group, the alkyl portion of the alkoxy, alkylthio and alkylamino groups may have one to three substituents selected from those recited above for substituted alkyl. The nitrogen atom of the alkylamino group may optionally be substituted with a group selected from alkyl, substituted alkyl, alkenyl, alkynyl, cyano, —SO$_2$(alkyl), —SO$_2$(aryl), —CO$_2$H, —C(=O)H, —CO$_2$-alkyl, —(C=O)alkyl, aryl, heteroaryl, heterocyclo, and cycloalkyl.

The alkoxy, alkylthio, or alkylamino groups may be monovalent or bivalent. By "monovalent" it is meant that the group has a valency (i.e., power to combine with another group), of one, and by "bivalent" it is meant that the group has a valency of two.

When the term "alkyl" is used as a suffix in conjunction with a second group, such as in "arylalkyl," "aminoalkyl," or "cycloalkylalkyl", it is meant that an alkyl group is used as a linker to the second group. Thus, for example, the term arylalkyl includes benzyl, phenylethyl, etc., and aminoalkyl includes the group —CH$_2$—CH$_2$—NH$_2$. In such a case, the referenced second group (e.g., aryl in arylalkyl) is as defined herein and thus may be substituted as set forth in these definitions.

The term "halogen" includes chloro, bromo, fluoro, and iodo.

The term "haloalkyl" means an alkyl having one or more halo substituents, e.g., including trifluoromethyl.

The term "haloalkoxy" means an alkoxy group having one or more halo substituents. For example, "haloalkoxy" includes —OCF$_3$.

The term "acyl" refers to a carbonyl group

linked to an organic radical including an alkyl, alkenyl, alkynyl, substituted alkyl, substituted alkenyl, or substituted alkynyl, as defined above. The organic radical to which the carbonyl group is attached may be monovalent (e.g., —C(=O)-alkyl), or bivalent (e.g., —C(=O)alkylene, etc.)

The term "alkoxycarbonyl" refers to a carboxy or ester group

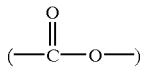

linked to an organic radical including an alkyl, alkenyl, alkynyl, substituted alkyl, substituted alkenyl, or substituted alkynyl, as defined above. The organic radical to which the carboxy group is attached may be monovalent (e.g., —CO$_2$-alkyl), or bivalent (e.g., —CO$_2$-alkylene, etc.)

The term "carbamyl" refers to —NR'—C(=O)R" or —C(=O)NR'R", wherein R' and R" may be hydrogen, alkyl, substituted alkyl, or cycloalkyl, as defined above.

The term "sulfonyl" refers to a sulphoxide group (i.e., —S(O)$_{1-2}$—) linked to an organic radical including an alkyl, alkenyl, alkynyl, substituted alkyl, substituted alkenyl, or substituted alkynyl group, as defined above. The organic radical to which the sulphoxide group is attached may be monovalent (e.g., —SO$_2$-alkyl), or bivalent (e.g., —SO$_2$-alkylene, etc.)

The term "sulfonamide" refers to the group —S(O)$_2$NR'R", wherein R' and R" may be hydrogen or alkyl, alkenyl, alkynyl, substituted alkyl, substituted alkenyl, or substituted alkynyl, as defined above. R' and R" may be monovalent or bivalent (e.g., —SO$_2$—NH-alkylene, etc.)

The term "cycloalkyl" refers to optionally-substituted fully saturated and partially unsaturated hydrocarbon rings of 3 to 9, preferably 3 to 7 carbon atoms. The term "cycloalkyl" includes such rings having zero, one, two, or three substituents, preferably zero or one, selected from the group consisting of halo, alkyl, substituted alkyl, alkenyl, alkynyl, nitro, cyano, amino, hydroxy, alkoxy, alkylthio, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —NH(alkyl), —NH(cycloalkyl), —N(alkyl)$_2$, —CO$_2$H, —C(=O)H, —CO$_2$-alkyl, —(C=O)alkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$—alkyl, keto, =N—OH, =N—O-alkyl, aryl, heteroaryl, heterocyclo, and a five or six membered ketal, i.e. 1,3-dioxolane or 1,3-dioxane. The term "cycloalkyl" also includes such rings having a bridge of 3 to 4 carbon atoms.

The term "aryl" refers to phenyl, biphenyl, 1-naphthyl and 2-naphthyl, with phenyl being preferred. The term "aryl" includes such rings having from zero, one, two or three substituents selected from the group consisting of halo, alkyl, substituted alkyl, alkenyl, alkynyl, nitro, cyano, amino, hydroxy, alkoxy, alkylthio, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —NH(alkyl), —NH(cycloalkyl), —N(alkyl)$_2$, —CO$_2$H, —C(=O)H, —CO$_2$-alkyl, —(C=O)alkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, cycloalkyl, heterocyclo, and heteroaryl.

When the term "aryl" is used with a hypen following another group, as in —O—C$_{0-2}$alkylene-aryl, —S—C$_{0-2}$alkylene-aryl, —N—C$_{0-2}$alkylene-aryl, acyl-aryl, alkoxycarbonyl-aryl, or sulfonamide-aryl, it is meant that the hypenated group or groups serve as a linker to the aryl. In such a case, the aryl may be unsubstituted or substituted with one to three groups, as defined above.

The term "heterocyclo" refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halo, alkyl, substituted alkyl, alkenyl, alkynyl, nitro, cyano, amino, hydroxy, alkoxy, alkylthio, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —NH(alkyl), —NH(cycloalkyl), —N(alkyl)$_2$, —CO$_2$H, —C(=O)H, —CO$_2$-alkyl, —(C=O)alkyl, —(C=O)NH$_2$, —(C=O)NH(alkyl), —(C=O)NH(cycloalkyl), —(C=O)NH(cycloalkyl), —(C=O)N(alkyl)$_2$, —NH—CH$_2$—CO$_2$H, —NH—CH$_2$—CO$_2$-alkyl, aryl, heteroaryl, heterocyclo, cycloalkyl, keto, =N—OH, =N—O-alkyl, and a five or six membered ketal, i.e., 1,3-dioxolane or 1,3-dioxane.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The aromatic portion of the heteroaryl ring system may contain zero, one, two or three substituents selected from the group consisting of halo, alkyl, substituted alkyl, alkenyl, alkynyl, nitro, cyano, amino, hydroxy, alkoxy, alkylthio, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —NH(alkyl), —NH(cycloalkyl), —N(alkyl)$_2$, —CO$_2$H, —C(=O)H, —CO$_2$-alkyl, —(C=O)alkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, cycloalkyl, heterocyclo, and heteroaryl. The non-aromatic portion of the heteroaryl ring may contain one or more of the above-referenced substituents as well as keto (=O), =N—OH, =N—O-alkyl, and the like.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "carbocyclic" refers to optionally substituted aromatic or non-aromatic 3 to 7 membered monocyclic and 7 to 11 membered bicyclic groups, in which all atoms of the ring or rings are carbon atoms.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds. Thus, for example, in compounds of formula (I), the substituent R$_3$ may be attached to any available carbon atom of the "A" ring, including the atom T to which the group R$_1$ is attached. For ease of reference, this atom may be referred to as the "R$_1$ substituted atom." When R$_1$ comprises a heteroatom directly attached to ring A, advantageously any R$_3$ group attached to T does not comprise a heteroatom directly attached to ring A, and vice-versa.

In compounds of formula (I), wherein R$_1$ and/or R$_3$ is attached to the 4-position atom of a piperazine ring (i.e., wherein M is N, A is a six-membered ring, and the fourth atom on the ring A [where M=atom 1] is a nitrogen atom), these groups preferably do not comprise "amine-protecting groups." More particularly, where ring A is

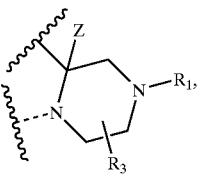

R$_1$ preferably is not an amine-protecting group. The term "amine-protecting group" as used herein refers to those groups that one skilled in the field would readily recognize as being suitable to protect the 4-position amine of a piperazinyl ring and which may be removed under typical deprotection conditions well known to those skilled in the field as set forth in Greene and Wuts, *Protecting Groups in Organic Synthesis* (John Wiley & Sons, New York 1991). For example, "amine-protecting group" includes those protecting groups disclosed in EP 1 004 583 A2, incorporated herein by reference, namely, Boc, CBZ, FMOC, benzyl, and ethyloxycarbonyl. The term "amine-protecting group" as used herein does not include —$C_{2-4}$alkyl; —$C_{1-4}$alkyl or $C_{3-7}$cycloalkyl substituted with —$CO_2H$, —$SO_2H$, aryl, heteroaryl, or tetrazole, i.e.,

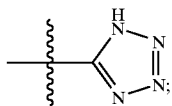

or $C_{2-4}$alkyl substituted with alkoxy, N(alkyl)$_2$, or heterocycle. The term "end-product substituent" means a substituent other than hydrogen that one skilled in the field would recognize is not an amine-protecting group as defined above. Thus, an "end-product substituent" includes —$C_{2-4}$alkyl; —$C_{1-4}$alkyl substituted with —$CO_2H$, —$SO_2H$, aryl, heteroaryl, or tetrazole; or $C_{2-4}$alkyl substituted with alkoxy, N(alkyl)$_2$, or heterocycle.

The compounds of formula (I) form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization. The inventive compounds may be in the free or hydrate form.

Preferred Compounds

Preferred compounds are those of formula (I) and/or pharmaceutically acceptable salts thereof:

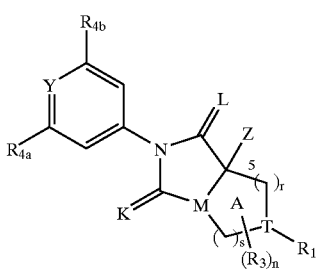

(I)

wherein
- A is a saturated, 4 to 7-membered monocyclic cycloalkyl or heterocycle;
- Y is CH;
- M is N or CH;
- L and K are O;
- Z is alkyl or substituted alkyl except when M is N, Z is not arylalkyl or heteroarylalkyl;
- either T is CH and $R_1$ is —$C_{0-2}$aekylene-aryl, —O—$C_{0-2}$alkylene-aryl, —S—$C_{0-2}$alkylene-aryl, —$NR_{10}$—$C_{0-2}$alkylene-aryl, acyl-aryl, oxy-carbonyl-aryl, or sulfonamide-aryl, or T is nitrogen and $R_1$ is —$C_{0-2}$alkylene-aryl, acyl-aryl, or alkoxycarbonyl-aryl;
- $R_3$ is alkyl, substituted alkyl, nitro, cyano, hydroxy, alkoxy, substituted alkoxy, amino, alkylamino, acyl, alkoxycarbonyl, carbamyl, sulfonyl, or sulfonamide;
- $R_{4a}$ and $R_{4b}$ are each halogen;
- $R_{10}$ is hydrogen, alkyl, or substituted alkyl;
- n is 0 or 1;
- r is 1 or 2; and
- s is 0, 1 or 2.

More preferred are compounds where n is 0 such that $R_3$ is absent.

Advantageously, in compounds of formula (I), where A is piperazine and $R_1$ is attached to the 4-position nitrogen atom of ring A (i.e., M is N, T is N, r is 1 and s is 2), $R_1$ is preferably —$C_2$alkylene-aryl; $R_1$ is not an amine-protecting group and thus is not benzyl or Boc.

More preferred compounds are those having formula (I), above, in which
- A is a saturated, 5 membered monocyclic ring (i.e., r and s are both 1);
- M is N or CH;
- L and K are both O;
- Y is CH;
- Z is hydrogen, lower alkyl, or lower alkyl substituted with hydroxy, lower alkoxy, or halogen,
- T is CH and $R_1$ is —$C_{0-2}$alkylphenyl, —O—$C_{0-2}$alkylene-phenyl, —S—$C_{0-2}$alkylene-phenyl, —$NR_{10}$—$C_{0-2}$alkylene-phenyl, acyl-phenyl, oxycarbonyl-phenyl, or sulfonamide-phenyl, or T is N and $R_1$ is —$C_{0-2}$alkylene-phenyl, acyl-phenyl, or alkoxycarbonyl-phenyl, and said $R_1$ phenyl group has zero or one substituent selected from halogen, $C_{1-4}$alkyl, nitro, cyano, hydroxy, $C_{1-4}$alkoxy, —$CO_2$H, —C(=O)H, amino, and alkylamino; and
- $R_{4a}$ and $R_{4b}$ are each chloro;
- $R_{10}$ is hydrogen or lower alkyl; and
- n is 0 such that $R_3$ is absent;

Most preferred compounds are (i) those having formula (Ia):

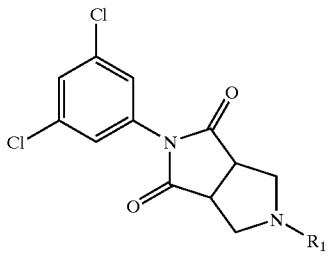

(Ia)

in which
$R_1$ is selected from

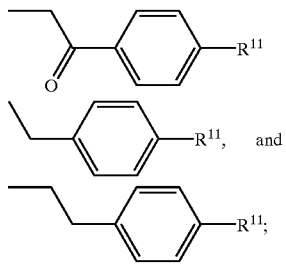

(ii) those having the formula (Ib):

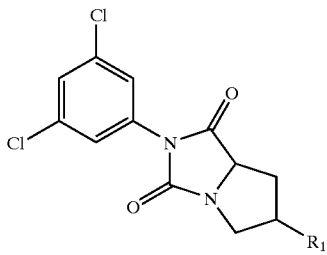

(Ib)

in which $R_1$ is selected from:

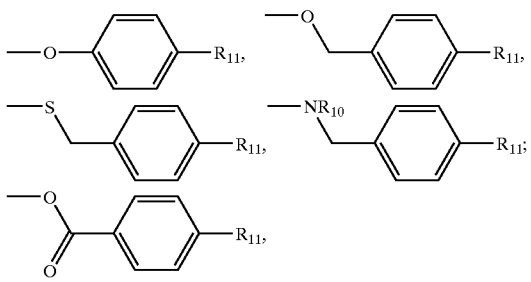

wherein in each of the compounds of formula (Ia) and (Ib), $R_{11}$ is selected from bromo, chloro, cyano, and methoxy, and $R_{10}$ is selected from hydrogen and alkyl.

Methods of Preparation

The compounds of the invention may be prepared by the exemplary processes described in the following reaction schemes A to J. Exemplary reagents and procedures for these reactions appear hereinafter. Starting materials are commercially available or can be readily prepared by one of ordinary skill in the art, and/or modifications can be made to the methods of Schemes A to J by one skilled in the art, using known methods. In the schemes, the groups $R_1$, $R_3$, K and Z are defined as recited in the claims. The group "$R_2$" is used for ease of reference to describe the left-hand phenyl ring recited in the claims. Groups designated R', R", Z, P', and P" as well as solvents, temperatures, pressures, and other reaction conditions, may readily be selected as appropriate by one of ordinary skill in the art.

In Scheme B, compound of formula (Ic) where $R_1$ is a benzyl group can be debenzylated to give the N-unsubstituted molecule 7. Depending on the nature of the group $R_2$, this step can be carried out through a catalytic hydrogenation over Pd/C in acetic acid or in alcohol, or by reaction with 1-chloroethyl chloroformate in DCM. Compound 7 can also be obtained by reaction of maleimide 3

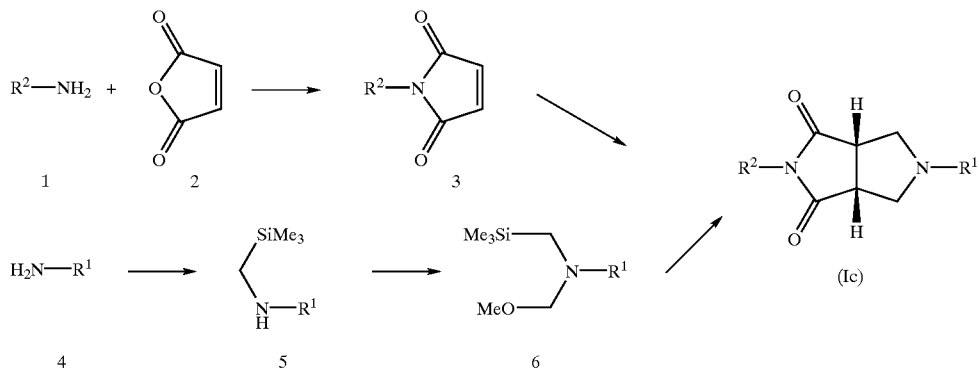

Scheme A

In Scheme A, an amine of formula 1 is reacted with maleic anhydride 2, as described for example in Org. Synth. (1961), 41, 93–5, to yield maleimide 3. An amine 4 is reacted with chloromethyltrimethylsilane to give trimethylsilylmethylamine 5. This procedure can be conveniently carried out in acetonitrile or in an alcohol in the presence of a base such as TEA, potassium or sodium carbonate. Amine 5 is then condensed with formaldehyde in the presence of MeOH to give methoxymethylamine 6. The latter can be condensed with maleimide 3 under acidic catalysis to give tetrahydropyrrolo[3,4-c]pyrrole-1,3-dione of formula (Ic). This reaction is carried out advantageously using a catalytic amount of TFA in DCM.

with oxazolidinone 8 in refluxing toluene yielding 9 which is deprotected under acidic conditions, as described in *Bull. Chem. Soc. Jpn.* Vol. 60 (1987), at pp. 4079–89. Compound 9 can then be substituted by various electrophiles such as alkyl halides, alkyl mesylates or tosylates, acyl chlorides, or sulfonyl chlorides to yield the desired compounds of formula (Ic). This compound can also be obtained by reductive amination of 7 with a suitably functionalized aldehyde or ketone in the presence of a reducing agent such as sodium triacetoxyborohydride in DCM or sodium cyanoborohydride in acetonitrile.

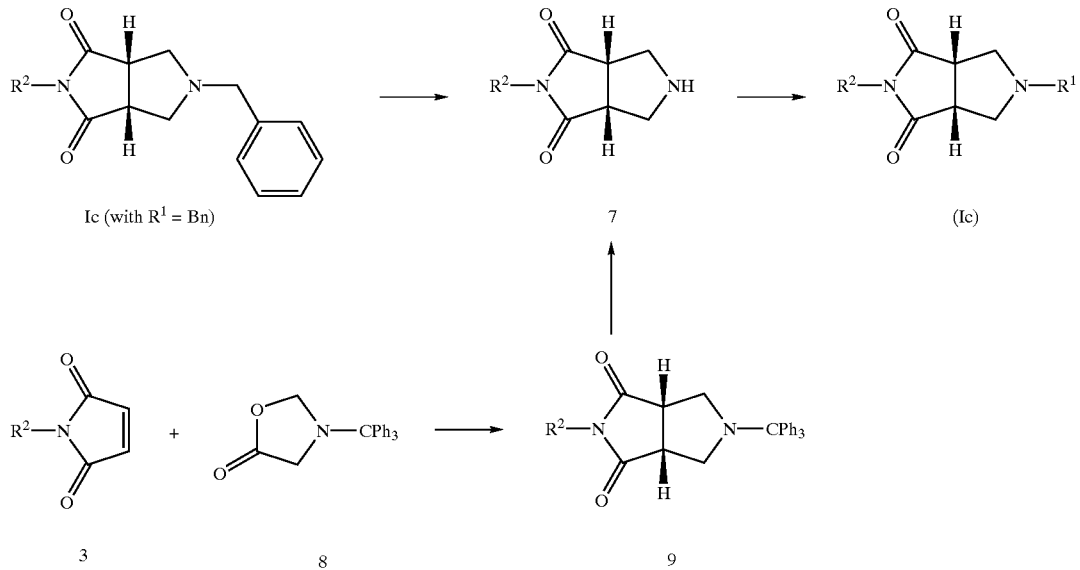

Scheme B

Scheme C

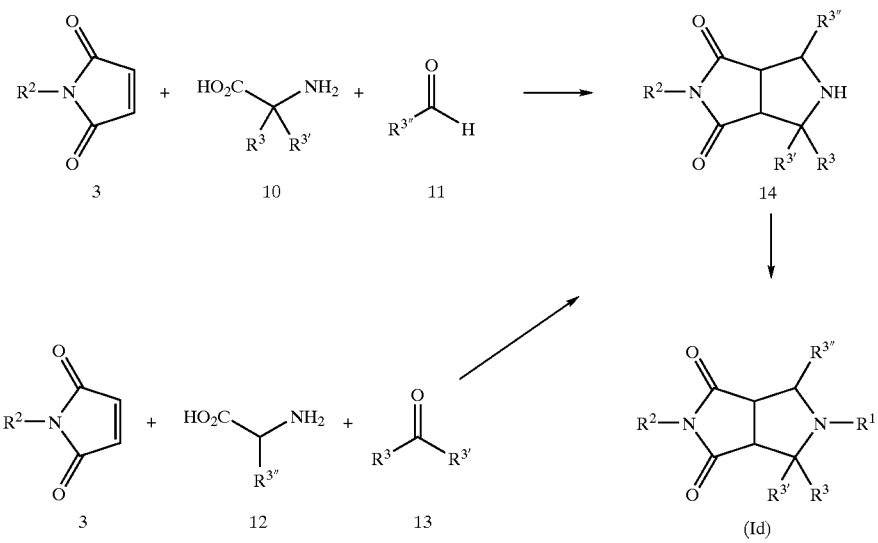

Substituted tetrahydro-pyrrolo[3,4-c]pyrrole-1,3-dione of formula (Id) can be obtained as depicted in Scheme C. Thus reaction of maleimide 3 with an aminoacid 10 and an aldehyde 11 in a solvent such as acetonitrile gives 14. This transformation is described in *J. Org. Chem.* Vo. 53 (1988), pp. 1384–91, and *Tetrahedron* Vol. 44 (1988), at 1523–34. The nitrogen atom of 14 can then be substituted under classical conditions to give the desired compound of formula (Id). The same type of substitution pattern can also be obtained by the reaction of maleimide 3 with an aminoacide 12 and a ketone 13 in DMF at 100° C. as described in *Tetrahedron Lett.* (1989), 30, at pp. 2841–44 or *Bull. Chem. Soc. Jpn.* (1987), 60, at pp. 4079–90.

Scheme D

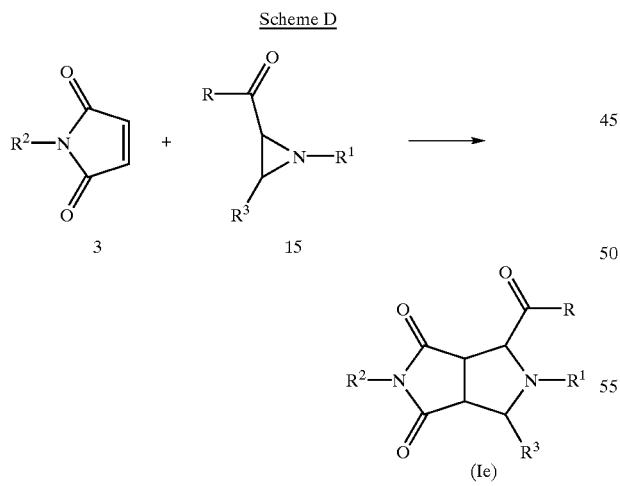

Tetrahydro-pyrrolo[3,4-c]pyrrole-1,3-dione of formula (Ie) substituted by a carbonyl group can be obtained by reacting maleimide 3 with aziridine 15 in toluene or xylene (Scheme D), as described in *J. Org. Chem.* (1988), 53, 1882–7 or in *Can. J. Chem.* (1970), 48, 2215–26.

Scheme E

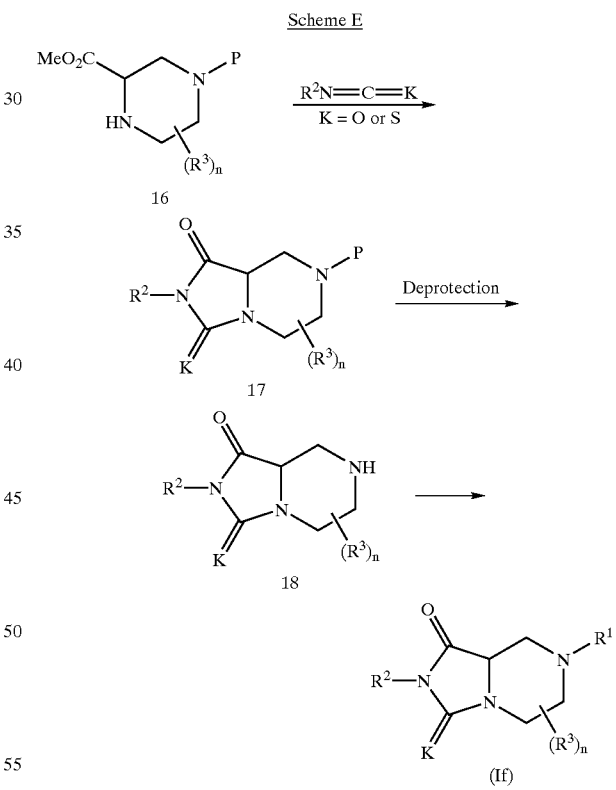

Compounds having the formula (If) can be prepared as described in Scheme E. The monoprotected piperazine carboxylic acid ester 16 (see, e.g., Hu et al. *Bioorg. Med. Chem. Lett.* (1999), 9, at pp. 1121–6) is reacted with either an isocyanate or an isothiocyanate in a solvent such as methylene chloride or DMF in the presence of a base such as potassium carbonate, sodium carbonate or TEA, to yield the hydantoin 17. The protecting group is removed to yield 18, which can then be further substituted by reaction with an electrophile (alkylation, acylation, reaction with a sulfonyl chloride, etc.) or by reductive amination to yield the desired compound of formula (If)

Scheme F

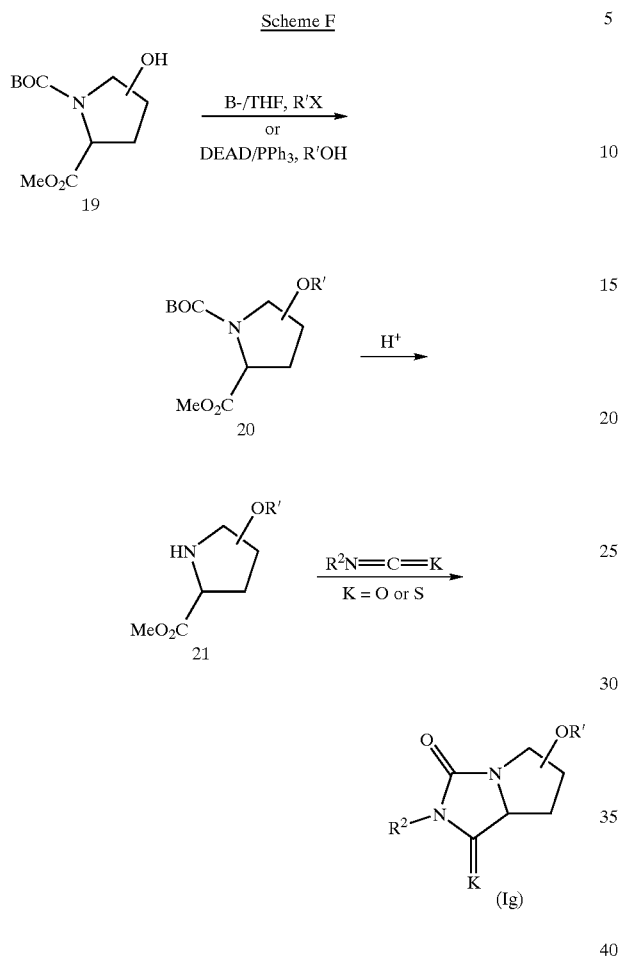

Protected hydroxy proline of formula 19 can be alkylated with R'X in the presence of a base such as NaH in THF (as described for example in *J. Med. Chem.*, [1988], 31(4), at pp. 875–885) or reacted with R'OH under Mitsunobu conditions (as described for example in *J. Med. Chem.*, [1988], 31(6), pp. 1148–1160) to give 20. Deprotection of 20 under acidic conditions yields 21, which is then cyclized with an isocyanate $R_2NCO$ or an isothiocyanate $R_2NCS$ in the presence of a base such as $K_2CO_3$ in a solvent such as DCM or DMF (as described for example in *Eur. J. Med. Chem.*, (1996), 31, pp. 717–713) to yield compounds of formula (Ig).

Scheme G

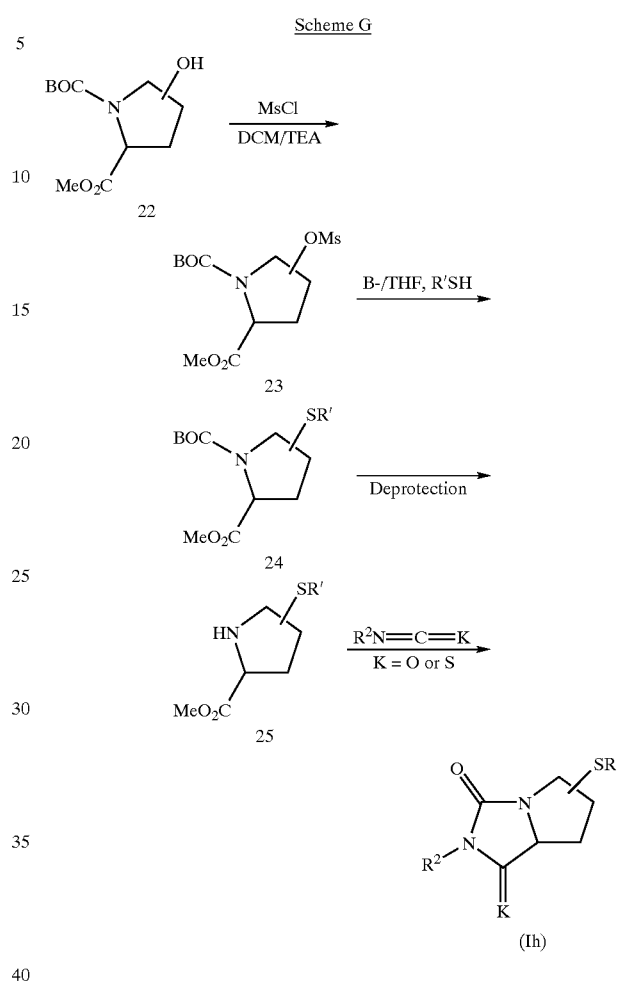

Protected hydroxy proline of formula 22 can be esterified with mesyl chloride then reacted with a thiol of formula R'SH in the presence of a base such as NaH in THF (as described for example in *J. Med. Chem.* (1988), 31(4), at pp. 875–885) to give the thioether 24. Thioether 24 is deprotected under acidic conditions to give 25. Cyclization of 25 with an isocyanate $R_2NCO$ or an isothiocyanate $R_2NCS$ in the presence of a base such as $K_2CO_3$ in a solvent such as DCM or DMF gives compounds of formula (Ih).

Scheme H

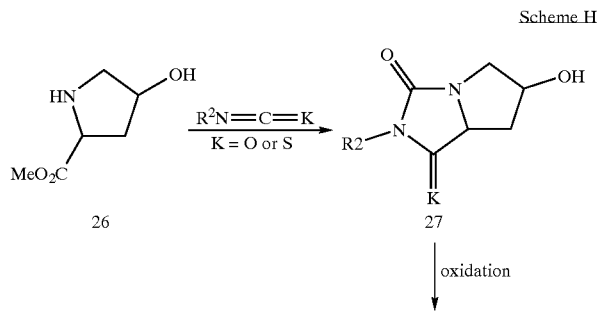

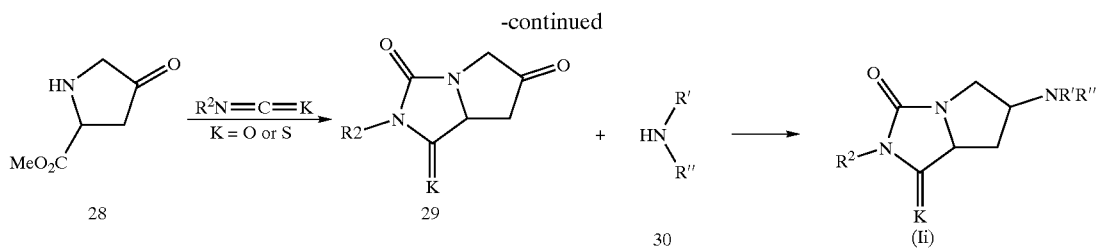

Hydroxy proline methyl ester of formula 26 can be cyclized with an isocyanate. R₂NCO or an isothiocyanate R₂NCS in the presence of a base such as K₂CO₃ in a solvent such as DCM or DMF to give 27. Compound 27 is oxidized in the presence of an oxidant such as pyridinium dichromate or Dess-Martin periodinane in DCM to give 29. Alternatively, oxo proline methyl ester of formula 28 (see for example, Bose, D. et al. *Tetrahedron Lett.*; 31; 47 [1990] at pp. 6903–6906) can be cyclized with an isocyanate R₂NCO or an isothiocyanate R₂NCS in the presence of a base such as K₂CO₃ in a solvent such as DCM or DMF to give the oxohydantoin 29. Reductive amination of 29 with an amine of formula 30 in the presence of a reducing agent such as sodium triacetoxyborohydride in DCM or sodium cyanoborohydride in acetonitrile under dehydrating conditions yields compounds of formula (Ii).

Scheme I

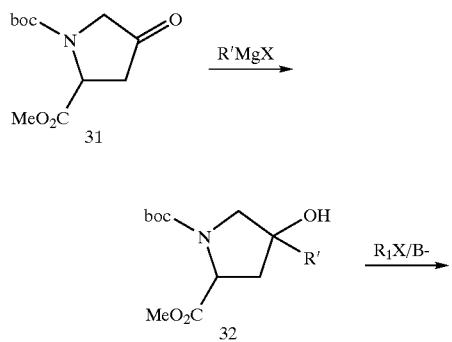

Protected oxo proline methyl ester of formula 31 (see for example, Barralough, P., et al., *Tetrahedron* (1995), 51(14), at pp. 4195–4212) can be reacted with a Grignard Reagent R'MgX (see for example, Tamaki M., et al., *J. Org. Chem.* (2001), 66, at pp. 3593–3596), to give 32. Compound 32 can be alkylated with R"X in the presence of a base to give 33, which is deprotected to give 34. Cyclization of 34 with an isocyanate R₂NCO or an isothiocyanate R₂NCS in the presence of a base such as K₂CO₃ in a solvent such as DCM or DMF gives compounds of formula (Ij).

Scheme J

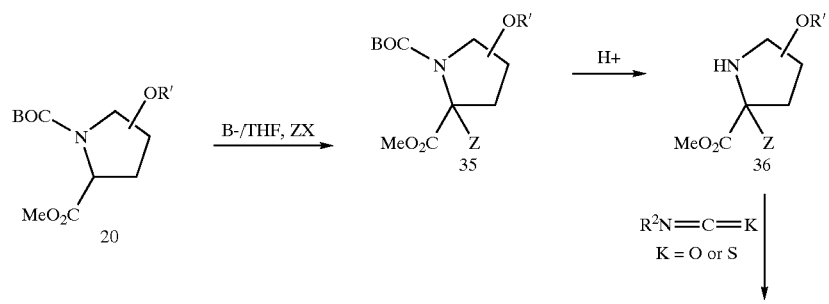

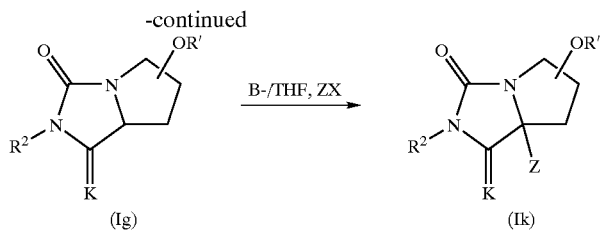

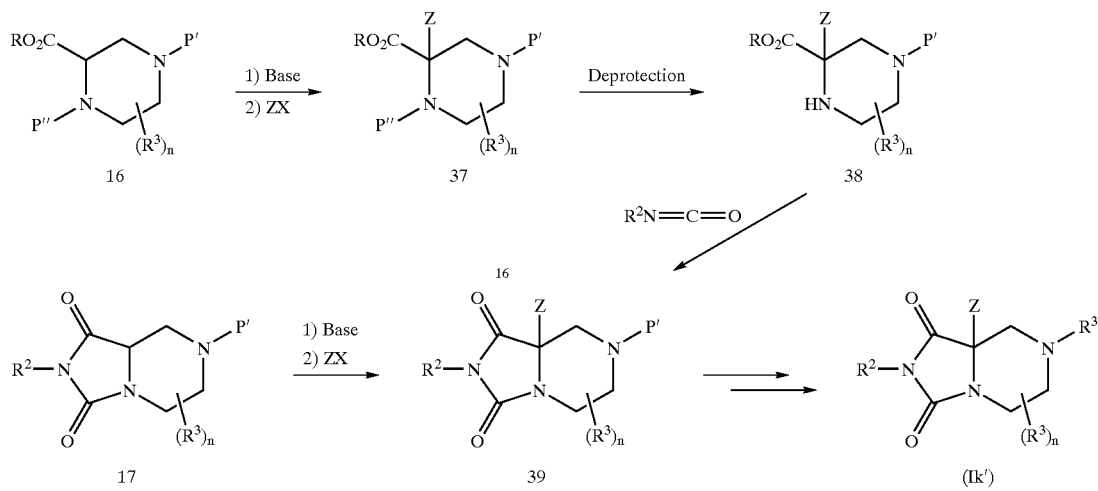

Protected substituted proline of formula 20 (Scheme J) can be alkylated with R'X in the presence of a base such as LDA or LiHMDS in THF (as described, for example, in Khalil, Ehab M. et al., *J. Med. Chem.*; [1999], 42(4), pp628–637) to give 35. After deprotection under acidic conditions, 36 is cyclized with an isocyanate $R_2NCO$ or an isothiocyanate $R_2NCS$ in the presence of a base such as $K_2CO_3$ in a solvent such as DCM or DMF (as described, for example, in *Eur. J. Med. Chem.*, (1996), 31, pp. 717–713) to yield compounds of formula (1k).

Alternatively, monocyclic compounds such as 16 (Scheme K) can be substituted with Z groups other than hydrogen prior to cyclization, e.g., by treatment at low temperature (−78° C.) in a solvent such as THF with a strong base such as LDA, potassium, lithium or sodium bis(trimethylsilyl)amide (KHMDS, LiHMDS, NaHMDS) to generate enolates which can be reacted with an electrophile ZX to give compounds having the desired Z groups.

The alkylation of other hydantoins to produce compounds of formula (Ik) or (Ik') wherein Z is other than hydrogen can be performed as described in Scheme J and K, e.g., with an alkyl halide in the presence of base such as LDA or LiHMDS in THF. See also Seebach et al., *J. Am Chem. Soc.*, Vol. 105(16) (1983) at pp. 5390–5398.

Each of the documents referenced above in the reactions schemes and hereinafter (e.g., in the Examples) is incorporated herein by reference.

EXAMPLES

The following Examples illustrate embodiments of the inventive compounds and starting materials, and are not intended to limit the scope of the claims. For ease of reference, the following abbreviations are used herein.

Abbreviations

Me=methyl
MeOH=methanol
Et=ethyl
EtOH=ethanol
Bn=benzyl
t-Bu=tert-butyl
Boc=tert-butoxycarbonyl
CBZ=carbobenzyloxy
CDI=1,1'-carbonyldiimidazole
DCM=dichloromethane
DEAD=diethyl azodicarboxylate
DIAD=diisopropyl azodicarboxylate
DMF=dimethyl formamide
DMSO=dimethylsulfoxide
EDC (or EDC.HCl) or EDCl (or EDCl.HCl) or EDAC=3-ethyl-3'-(dimethylamino)propyl-carbodiimide hydrochloride (or 1-(3-dimethylaminopropyl)-3-ethylcarbodiimide hydrochloride)
EtOAc=ethyl acetate
FMOC=9-fluorenylmethyl carbamate
HOBT=1-hydroxybenzotriazole hydrate
HYP=trans-L-4-hydroxy-proline
KHMDS=potassium bis(trimethylsilyl)amide
LDA=lithium diisopropylamide
LiHMDS=lithium hexamethyldisilazane
$NaBH(OAc)_3$=sodium triacetoxyborohydride
PDC=pyridinium dichromate
Pet.=petroleum
Ph=phenyl
$Ph_3P$=triphenylphosphine
TEA=triethylamine
TFA=trifluoroacetic acid
THF=tetrahydrofuran L=liter
mL=milliliter
μL=microliter
g=gram(s)
mg=milligram(s)
RT=room temperature
HPLC=high performance liquid chromatography
Mp=melting point Preparation 1

Trans-1-(3,5-dichloro-phenylcarbamoyl)-4-hydroxy-L-proline (2S,4R)

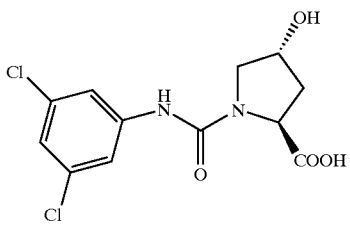

To a solution of HYP (1 g) (0.0076 mol) and KOH (1.05 g) (1 eq.) in 10 mL of water was added 3,5-dichlorophenyl isocyanate (1.42 g) (1 eq.) in portions. The reaction was stirred overnight and the insoluble material removed by filtration. The aqueous phase was acidified with dilute HCl and extracted with EtOAc. The combined organic extracts were washed with water, dried over MgSO$_4$, and evaporated under reduced pressure to afford the above-titled compound as a white solid (1.8 g). NMR (CDCl$_3$, 200 MHz): 8.7 (1H, NH), 7.65 (2H, d), 7.15 (1H, m), 5.2 (1H, OH), 4.25–4.45 (2H, m), 3.65 (1H, dd), 3.42 (1H, d), 2.05–2.25 (1H, m), 1.85–2.05 (1H, m).

Preparation 2

(7aS,6R)-2-(3,5-dichloro-phenyl)-6-hydroxy-tetrahydro-pyrrolo[1,2-c]imidazole-1,3-dione

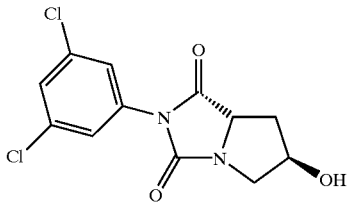

1-(3,5-dichloro-phenylcarbamoyl)-4-hydroxy-L-proline (6.8 g) (0.021 mol) (Preparation 1) was combined with 35 mL of 1 N HCl and refluxed for 11 hrs. The organic oil was separated from the reaction mixture and dissolved in EtOAc. The organic layer was washed with water, dried over MgSO$_4$, and evaporated under reduced pressure. The resulting residue was purified on a SiO$_2$ column (eluent: DCM/acetone-90/10) to afford the titled compound as a white solid (3.2 g). NMR (CDCl$_3$, 200 MHz): 7.4 (2H, d), 7.35 (1H, m), 4.75 (1H, m), 4.60 (1H, dd), 3.95 (1H, dd), 3.35 (1H, d), 2.75 (1H, m, OH), 2.40 (1H, dd), 1.80–1.95 (1H, m).

Preparation 3

(7aS,6S)-2-(3,5-dichloro-phenyl)-6-hydroxy-tetrahydro-pyrrolo[1,2-c]imidazole-1,3-dione

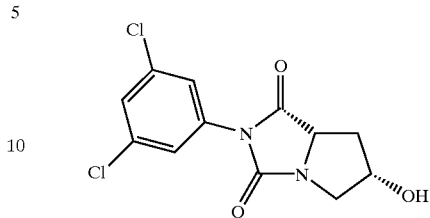

To a solution of cis-4-hydroxy-L-proline methyl ester (0.53 g) (0.0036 mol) in 10 mL of DMF cooled at 0° C. was added K$_2$CO$_3$ (0.52 g) (1.1 eq.), then 3,5-dichlorophenyl isocyanate (0.75 g) (1.1 eq.). The reaction was stirred overnight at RT and the insoluble material removed by filtration. The solution was concentrated under vacuum and the residue dissolved in DCM. The organic layer was washed with water, dried over MgSO$_4$, and evaporated under reduced pressure. The resulting residue was purified on a SiO$_2$ column (eluent: DCM/acetone-95/5) to afford the titled compound as a white solid (0.25 g). NMR (CDCl$_3$, 200 MHz): 7.35 (3H, s), 4.45 (1H, m), 4.30 (1H, dd), 4.0 (1H, d), 3.1 (1H, dd), 2.35–2.2 (2H, m), 1.95 (1H, bs, OH).

Preparation 4

Cis-4-(4-bromo-phenoxy)-L-proline methyl ester (4S,2S)

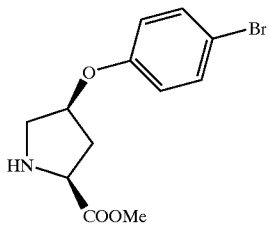

To a solution of trans-1-(Boc)-4-hydroxy-L-proline methyl ester (0.5 g) (2 mmol), 4-bromophenol (0.52 g) (1.5 eq.) and Ph$_3$P (0.78 g) (1.5 eq.) in 10 mL of dry THF at 0° C. was added DEAD (0.47 mL) in a minimal volume of THF. The reaction mixture was warmed to RT overnight. The solvent was removed in vacuo and the resulting residue suspended in ether. The solids were removed by filtration and the solvent evaporated under reduced pressure to afford after SiO$_2$ chromatography (eluent: cyclohexane/EtOAc-9/1), cis-1-(Boc)-4-(4-bromo-phenoxy)-L-proline methyl ester as a colorless oil (0.54 g). NMR (CDCl$_3$, 200 MHz): 7.37 (2H, d), 6.70 (2H, d), 4.85 (1H, m), 4.37–4.6 (1H, m), 3.6–3.85 (5H, m), 2.35–2.50 (2H, m), 1.4–1.5(9H). To a solution cis-1-(Boc)-4-(4-bromo-phenoxy)-L-proline methyl ester (0.54 g) in 8 mL of DCM at 0° C. was added 2.5 mL of TFA. The reaction mixture was stirred at 0° C. for 1 h and warmed to RT for an additional hour. The solvents were evaporated in vacuo. The resulting residue was dissolved in water and the aqueous layer basified with aqueous NaHCO$_3$ and extracted with EtOAc. The combined organic extracts were washed with water, dried over MgSO$_4$, and the solvent was evaporated under reduced pressure to afford the titled compound as a colorless oil which solidified upon standing (0.39 g). NMR (CDCl$_3$, 200 MHz): 7.35 (2H, d), 6.70 (2H, d), 4.8 (1H, m), 3.92 (1H, dd), 3.72 (3H, s), 3.35 (1H, d), 3.1 (1H, dd) 2.25–2.55 (2H, m).

Preparation 5

Trans-4-(4-bromo-benzyloxy)-L-proline methyl ester (2S,4R)

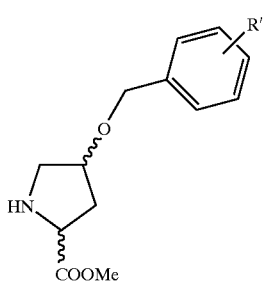
(P5)

The compound of formula (P5), wherein R' is 4-Bromo and the bonds linking the benzyloxy and methyl ester groups (depicted in P5 as wavy bonds) define the trans, L-proline configuration (2S,4R) was prepared as follows. To a suspension of sodium hydride (60% in oil) (0.12 g) (1.5 eq.) in 5 mL of dry THF was added trans-N-Boc-4-hydroxy-L-proline methyl ester (0.5 g) in 5 mL of dry THF. The reaction mixture was stirred for 45 minutes and a solution of 4-bromobenzyl bromide (0.75 g) (1.5 eq.) in 5 mL of dry THF was added. The reaction mixture was refluxed for 3 hours. After cooling to RT, the reaction mixture was diluted with water and extracted with EtOAc. The aqueous layer was acidified and extracted with DCM. The combined organic extracts were washed with water, dried over $MgSO_4$, and evaporated under reduced pressure to afford trans-N-Boc-4-(4-bromo-benzyloxy)-L-proline (0.25 g). NMR ($CDCl_3$, 200 MHz): 7.47 (2H, d), 7.2 (2H, d), 4.50–4.30 (3H, m), 4.25–4.1 (1H, m), 3.75 (3H, s), 3.8–3.5 (2H, m), 2.5–2.3 (1H, m), 2.15–1.95 (1H, m), 1.5–1.35 (9H).

$SOCl_2$ (0.27) was carefully added dropwise to 2.7 mL of MeOH at −5° C. To this mixture was added trans-N-Boc-4-(4-bromo-benzyloxy)-L-proline (0.25 g) in 2.7 mL of MeOH. The reaction mixture was allowed to warm to 20° C. and stirred overnight. The solvent was evaporated under reduced pressure and the residue dissolved in DCM. The organic layer was washed with water, dried over $MgSO_4$, and evaporated in vacuo to afford the above-titled compound (60 mg). NMR ($CDCl_3$, 200 MHz): 7.45 (2H, d), 7.2 (2H, d), 4.44 (2H, s), 4.15–4.05 (1H, m), 4.0 (1H, t), 3.7 (3H, s), 3.2–3.05 (2H,m), 2.27 (1H, dd), 2.05–1.9 (1H, m).

Preparations 6–8

Compounds having the above formula (P5), wherein R' has the values listed in Table 1 and the wavy bonds linking the benzyloxy and methyl ester groups define the isomers identified in Table 1, were produced using the same or similar method as for Preparation 5.

TABLE 1

| Example No. | R' | Stereo isomer | NMR ($CDCl_3$, 200 MHz) |
|---|---|---|---|
| 6 | 4-Br | Cis,L (2S,4S) | 7.35 (2H,d), 7.05 (2H,d), 4.3 (2H,s), 4.15–3.9 (1H,m), 3.72 (1H,t), 3.65 (3H,s), 3.15 (1H,d), 2.85 (1H,dd), 2.25–2.1 (2H,m). |

TABLE 1-continued

| Example No. | R' | Stereo isomer | NMR ($CDCl_3$, 200 MHz) |
|---|---|---|---|
| 7 | 4-(2-CN Phe) | Cis,L (2S,4S) | 7.7–7.3 (8H,m), 4.4 (2H,s), 4.1–3.95 (1H,m), 3.70 (1H,dd), 3.60 (3H,s), 3.5 (NH), 3.20 (1H,d), 2.4 (1H,dd), 2.10–2.30 (2H,m) |
| 8 | 3-Br | Cis,L (2S,4S) | 7.5–7.35 (2H,m), 7.25–7.15 (2H,m), 4.4 (2H,s), 4.1–4.0 (1H,m), 3.35–3.2 (4H,m), 3.25 (1H,d), 2.90 (1H,dd), 2.6 (NH), 2.3–2.2 (2H,m) |

Preparation 9

Trans-N-Boc-4-methanesulfonyloxy-L-proline methyl ester (2S,4R)

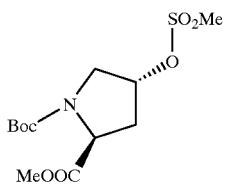

To a solution of trans-N-Boc-4-hydroxy proline methyl ester (17.6 g) (0.072 mol) and TEA (12.5 mL) (0.09 mol) in 100 mL of DCM at 0° C. was slowly added methanesulfonyl chloride (7 mL) (0.09 mol). The temperature was allowed to warm to 20° C., and the mixture was stirred overnight. Insoluble material was removed by filtration and the organic layer washed with water, dried over $MgSO_4$, and evaporated in vacuo to afford the above-titled compound as an oil which solidified upon standing (24 g). NMR($CDCl_3$, 200 MHz): 5.22 (1H, m), 4.32–4.5 (1H, m), 3.5–3.9 (5H, m), 3.05 (3H, s), 2.5–2.73 (1H, m), 2.15–2.35 (1H, m), 1.35–1.5 (9H).

Preparation 10

Cis-4-(4-bromobenzyl thio)-L-proline methyl ester (2S,4S)

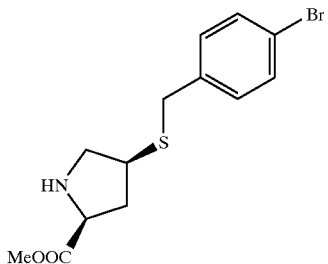

To a solution of Na (0.25 g) (0.011 mol) in 3 mL of MeOH was added 4-bromobenzyl mercaptan (2.2 g) (0.011 mol). The reaction mixture was stirred for 1 h. Trans-N-Boc-4-methanesulfonyloxy-L-proline methyl ester (1.2 g) (0.0037 mol) (Preparation 9) was added and the mixture refluxed for 18 hrs. Upon cooling to RT, 40 mL of water was added and the mixture was extracted with EtOAc. The aqueous layer was acidified with 1 N HCl and extracted with DCM. The combined organic extracts were washed with water, dried over $MgSO_4$, and the solvent evaporated in vacuo to afford cis-N-Boc-4-(4-bromobenzyl thio)-L-proline (1.08 g). NMR (CDCl₃, 200 MHz): 10.65 (1H, COOH), 7.4 (2H, d), 7.15 (2H, d), 4.15–4.35 (1H, m), 3.65 (2H, s), 2.95–3.35 (2H, m), 2.4–2.6 (1H, m), 1.85–2.2 (1H, m), 1.3–1.5 (9H). To a solution of cis-N-Boc-4-(4-bromobenzyl thio)-L-proline (1.08 g) in 10 mL of MeOH was added dropwise SOCl₂ (0.2 mL), and the mixture was stirred for 72 hrs at RT. The solvent was evaporated under reduced pressure and the residue dissolved in DCM. The organic layer was washed with dilute aqueous NaHCO₃, water, and dried over MgSO₄. The solvent was evaporated in vacuo to afford cis-4-(4-bromo-benzylthio)-L-proline methyl ester (0.6 g).

Preparation 11

4-Chloro-N-[(trimethylsilyl)methyl]benzeneethanamine

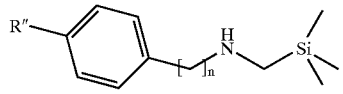
(P11)

The compound of formula (P11), wherein n=2 and R" is chloro, was prepared from a mixture of chloromethyltrimethylsilane (3.7 mL, 42.8 mmol), 2-(4-chlorophenyl)ethylamine (10 g, 64.25 mmol), and K₂CO₃ (4 g, 28.9 mmol) in acetonitrile (80 mL). The reaction mixture was refluxed for 13 h and after cooling, the precipitate was filtered off and the filtrate concentrated under vacuum. The resulting oil was chromatographed over silica gel (CH₂Cl₂/MeOH/Et₃N: 97/2/1) to yield the above-referenced compound as a colorless oil (5.17 g). ¹H NMR (CDCl₃): 7.25 (2H, d, J=8.3 Hz), 7.12 (2H, d, J=8.3 Hz), 2.7–2.9 (4H, m), 2.08 (3H, s), 0.95 (1H, br s), 0.02 (9H, s).

Preparations 12–13

Compounds having the formula (P11), wherein n=1 and R" has the values listed in Table 2, were produced using the same or similar method as for Preparation 11, starting with an appropriately-substituted benzylamine.

TABLE 2

| Preparation No. | R" | ¹H NMR (CDCl₃) |
| --- | --- | --- |
| 12 | OMe | 7.23 (2H,d,J=8.6 Hz), 6.87 (2H,d,J= 8.6 Hz), 3.80 (3H,s), 3.73 (2H,s), 2.03 (2H,s), 1.42 (1H,br s), 0.03 (9H,s). |
| 13 | Br | 7.40 (2H,d,J=8.4 Hz), 7.15 (2H,d,J= 8.4 Hz), 3.70 (2H,s), 1.97 (2H,s), 1.22 (1H,br s), 0.02 (9H,s). |

Preparation 14

4-Chloro-N-(methoxymethyl)-N-[(trimethylsilyl)methyl]benzeneethanamine

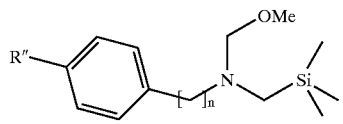
(P14)

The compound of formula (P14), in which n=2 and R" is chloro, was prepared from 4-chloro-N-[(trimethylsilyl)methyl]benzeneethanamine (5.17 g, 21.38 mmol) (Preparation 11), added dropwise to ice-cooled aqueous formaldehyde (37% w/v, 2.3 g, 28.34 mmol). After 10 min., MeOH (3 mL, 74 mmol) was added and the mixture stirred at 0° C. for 3 h. Anhydrous K₂CO₃ (1 g) was then added and the mixture stirred for 30 min at 0° C. The layers were separated and the aqueous phase extracted with τ-Bu methyl ether. The combined organic layers were dried over MgSO₄ and concentrated to yield the titled compound as a pale yellow oil (6.35 g). ¹H NMR (CDCl₃): 7.21 (2H, d, J=8.4 Hz), 7.09 (2H, d, J=8.4 Hz), 4.03 (2H, s), 3.21 (3H, s), 2.8–2.9 (2H, m), 2.65–2.8 (2H, m), 2.22 (2H, s), 0.03 (9H, s).

Preparations 15–16

Compounds having the formula (P14), wherein n=1 and R" has the values listed in Table 3, were produced using the same or similar method as for Preparation 14, starting with an appropriately-substituted N-[(trimethylsilyl)methyl]benzylamine.

TABLE 3

| Preparation No. | R" | ¹H NMR (CDCl₃) |
| --- | --- | --- |
| 15 | OMe | 7.24 (2H,d,J=8.4 Hz), 6.85 (2H,d,J= 8.4 Hz), 3.99 (2H,s), 3.80 (3H,s), 3.23 (3H,s), 2.18 (2H,s), 0.05 (9H,s). |
| 16 | Br | 7.40 (2H,d,J=8.4 Hz), 7.15 (2H,d,J= 8.4 Hz), 3.96 (2H,s), 3.68 (2H,s), 3.20 (3H,s), 2.12 (2H,s), 0.02 (9H,s). |

Preparation 17

2-(3,5-dichlorophenyl)-tetrahydro-pyrrolo[3,4-c]pyrrole-1,3(2H,3aH)-dione

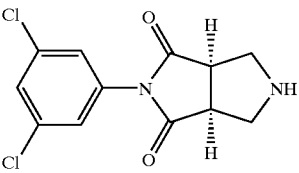

A solution of 5-benzyl-2-(3,5-dichlorophenyl)-tetrahydro-pyrrolo[3,4-c]pyrrole-1,3(2H,3aH)-dione (1.13 g, 3 mmol) in acetic acid (20 mL) was hydrogenated at atmospheric pressure over platinum oxide for 4 h. The catalyst was filtered off and the filtrate was poured into an ammonium hydroxide solution. The aqueous solution was extracted twice with methylene chloride. The organic layer was dried over sodium sulfate and concentrated in vacuo to give an oil (0.86 g) which was chromatographed over silica gel (CH₂Cl₂/MeOH/NH₄OH: 90/9/1) to yield the above compound as a white solid (0.53 g). Mp=170° C. ¹H NMR (DMSO-d₆): 7.73 (1H, m), 7.47 (2H, m), 3.2–3.5 (4H, m), 2.8–2.9 (2H, m).

Preparation 18

2-(3,5-Dichlorophenyl)-1,3-dioxo-hexahydro-imidazo[1,5-a]pyrazine-7-carboxylic acid tert-butyl ester

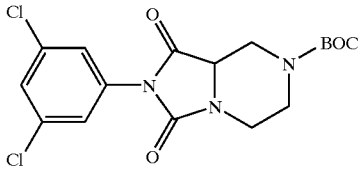

3,5-Dichlorophenyl isocyanate (2.85 g, 15.2 mmol) was added portionwise to a mixture of piperazine-1,3-dicarboxylic acid 1-tert-butyl ester 3-ethyl ester (2.61 g, 10.1 mmol, prepared as described in *Bioorg. Med. Chem. Lett.* 1999, 9, 1121–6) and potassium carbonate (1.68 g, 12.1 mmol) in DCM (30 mL) at 5° C. After 30 min at 5° C., the reaction mixture was stirred at 20° C. for 48 h. The white precipitate was discarded and the filtrate concentrated in vacuo to give an oil (5.5 g) which was chromatographed over silica gel ($CH_2Cl_2$), to yield the above compound (2.77 g) as a white solid. Mp=144° C.

Preparation 19

2-(3,5-Dichlorophenyl)-tetrahydro-imidazo[1,5-a]pyrazine-1,3-dione

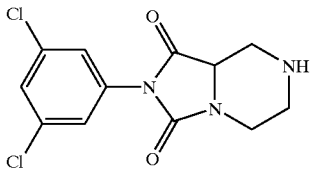

Methanesulfonic acid (2.1 mL, 32.7 mmol) was added to an ice-cold solution of 2-(3,5-Dichlorophenyl)-1,3-dioxo-hexahydro-imidazo[1,5-a]pyrazine-7-carboxylic acid tert-butyl ester (2.62 g, 6.54 mmol, Prep. 18) in methylene chloride (50 mL). After 1 h at RT, TEA (5 mL, 36 mmol) was added. The reaction mixture was washed twice with water, dried over sodium sulfate and concentrated in vacuo to yield the above compound (1.7 g) as a white solid. Mp=134° C. (crystallized from diethyl ether).

Preparation 20

(7aS)-2-(3,5-dichloro-phenyl)-tetrahydro-pyrrolo[1,2-c]imidazole-1,3,6-trione

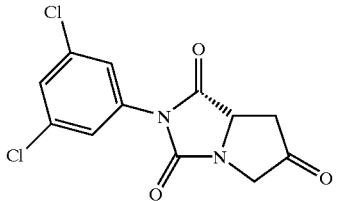

To a solution of (7aS,6R)-2-(3,5-dichloro-phenyl)-6-hydroxy-tetrahydro-pyrrolo[1,2-c]imidazole-1,3-dione (11.3 g) (0.038 mol) (Preparation 2), in 185 mL of DCM was added molecular sieves 3A (18 g) then PDC (33.5 g) (0.093 mol). The reaction mixture was stirred for 72 h at RT, then the insoluble material eliminated. After evaporating the solvent, the residue was purified by $SiO_2$ chromatography (eluent: DCM/EtOAc 95/5) to afford the titled compound as a white solid (7.3). NMR ($CDCl_3$, 200 MHz): 7.45–7.35 (3H, m), 4.65 (1H, dd), 4.25 (1H, dd), 3.12 (1H, dd), 2.97 (1H, dd), 2.65 (1H, dd).

Preparation 21

(2S,4S)-4-[(4-cyanophenyl)methoxy]-1,2-pyrrolidine-dicarboxylic acid 1-tert-butyl 2-methyl ester

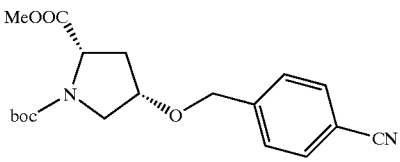

To a solution of trans-N-Boc-4-hydroxy-L-proline methyl ester (1.0 g) (4 mmol) and 4-bromomethyl benzonitrile (0.8 g) (4 mmol) in 20 mL of dry DMSO was added powdered KOH (0.23 g) (4.5 mmol) in portions. The mixture was stirred 4 hours at RT then poured in 100 mL of water and extracted with 150 mL of EtOAc. The organic layer was washed twice with water, dried over sodium sulfate and concentrated in vacuo to yield an oily residue (1.4 g) which was purified by $SiO_2$ chromatography (eluent: DCM/MeOH 95/5) to afford the titled compound (0.4 g). NMR ($CDCl_3$, 200 MHz): 7.6 (2H, d), 7.4 (2H, d), 4.55 (2H, s), 4.4 (1H, m), 4.15 (1H, m), 3.7–3.55 (5H, s+m), 2.5–2.25 (2H, m), 1.5–1.4 (9H). The compound was thensolubilized in 10 mL of DCM and treated with 0.8 mL of TFA at 0° C. The mixture was stirred overnight at RT then washed with a dilute aqueous solution of $NaHCO_3$, then water, dried over sodium sulfate and concentrated in vacuo to afford the titled compound (0.26 g) as an oil. NMR ($CDCl_3$, 200 MHz): 7.55 (2H, d), 7.3 (2H, d), 4.45 (2H, s), 4.0 (1H, m), 3.6 (3H, s), 3.25–3.1 (1H, m), 2.9–2.7 (2H, m), 2.25–2.1 (2H, m).

Preparation 22

(S)-2-(3,5-diChloro-phenyl)-10,10a-dihydro-5H-imidazo-[1,5-b]isoquinoline-1,3-dione

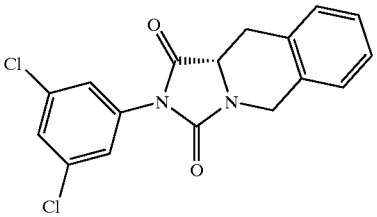

To a solution of L-tetrahydroisoquinoline-3-carboxylic acid, hydrochloride (0.5 g) (2.3 mmol) and $K_2CO_3$ (0.65 g) (2 eq.) in water (20 mL) was added finely powdered 3,5-dichlorophenyl isocyanate (0.44 g) (1 eq.). The reaction mixture was stirred for 48 h at RT, extracted with t-Bu methyl ether, and acidified with 1N HCl. The resulting solid was filtrated, washed with water, then dried to give 0.44 g of 1-(3,5-dichloro-phenylcarbamoyl)-L-tetrahydroisoquinoline-3-carboxylic acid. (Mp=234° C., NMR: $CHCl_3$, 200 MHz, 8.6 (1H, NH), 7.6 (2H, d), 7.2 (4H, m), 6.95 (1H, m), 5.25 (1H, m), 4.8 (2H, dd), 3.1–3.45 (2H, m)). The carboxylic acid (0.44 g) was suspended in dry toluene and conc. $H_2SO_4$ (0.1 mL) added. The resulting reaction mixture was heated to reflux until a clear solution was obtained. Insoluble material was removed by filtration and the solution cooled to precipitate the cyclized compound. The solid was collected by filtration to afford the titled compound (0.37 g). Mp=243° C., NMR ($CHCl_3$, 200 MHz): 7.45 (2H, d), 7.35 (1H, m), 7.25 (4H, m), 5.1 (1H, d), 4.5 (1H, d), 4.25 (1H, dd), 3.35 (1H, dd), 3.0 (1H, dd).

Preparation 23

(2S,4R)-4-(4-Bromobenzyloxy)-2-methyl-proline methyl ester

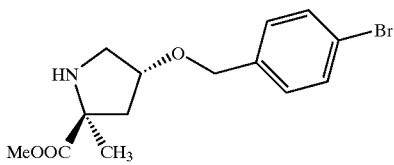

To a suspension of sodium hydride (60% in oil) (0.12 g) (1.5 eq.) in 5 mL of dry THF was added (2S,4R)-N-Boc-4-hydroxy-2-methyl-proline methyl ester (0.55 g) in 5 mL of dry THF. The reaction mixture was stirred for 45 min., and a solution of 4-bromobenzyl bromide (0.75 g) (1.5 eq.) in 5 mL of dry THF was added. The reaction mixture was refluxed for 3 h. After cooling to RT, the reaction mixture was diluted with water and extracted with EtOAc. The aqueous layer was acidified and extracted with DCM. The combined organic extracts were washed with water, dried over $MgSO_4$ and evaporated under reduced pressure to afford (2S,4R)-N-Boc-4-(4-bromo-benzyloxy)-2-methyl-proline (0.25 g).

$SOCl_2$ (0.27 mL) was carefully added dropwise to 2.7 mL of MeOH at −5° C. To this mixture was added (2S,4R)-N-Boc-4-(4-Bromobenzyloxy)-2-methyl-proline (0.25 g) in 2.7 mL of MeOH. The reaction mixture was allowed to warm to 20° C. and stirred overnight. The solvent was evaporated under reduced pressure and the residue dissolved in DCM. The organic layer was washed with water, dried over $MgSO_4$, and evaporated in vacuo to afford the titled compound (85 mg).

Example 1

(7aS,6S)-2-(3,5-dichloro-phenyl)-6-(4-bromophenoxy)-tetrahydro-pyrrolo[1,2-c]imidazole-1,3-dione

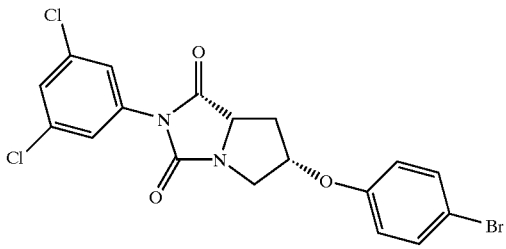

To a solution of (7aS,6R)-2-(3,5-dichloro-phenyl)-6-hydroxy-tetrahydro-pyrrolo[1,2-c]imidazole-1,3-dione (0.5 g) (1.67 mmol) (Preparation 2), $Ph_3P$ (0.44 g) (1eq.) and 4-bromophenol (0.29 g) (1 eq.) in 5 mL of dry THF at 0° C. was added DIAD (0.337 g) in a minimal volume of THF. The reaction mixture was warmed to RT overnight. After evaporating the solvent, the residue was dissolved in DCM, washed with $NaHCO_3$ solution, water, dried over $MgSO_4$, and the solvent was evaporated under reduced pressure, to afford after $SiO_2$ chromatography (eluent: DCM) the titled compound as a white solid (50 mg). Mp=116° C. NMR (DMSO, 200 MHz): 7.75 (1H, m), 7.5–7.4 (4H, d+d), 6.85 (2H, d), 5.1 (1H, m), 4.6 (1H, dd), 3.95 (1H, dd), 3.35 (1H, dd), 2.7–2.5 (1H, m), 2.25 (1H, bd).

Example 2

(7aS,6S)-2-(3,5-dichloro-phenyl)-6-(4-bromophenoxy)-tetrahydro-pyrrolo[1,2-c]imidazole-1,3-dione

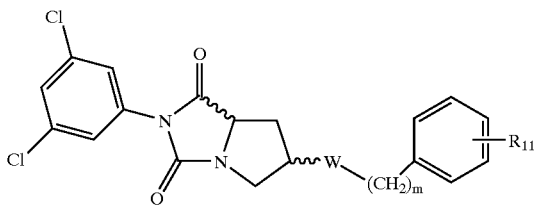

(II)

The compound of formula (II), wherein $R_{11}$ is 4-bromo, m is 0, W=O, and the bonds depicted as wavy bonds define the 7aS,6S stereoisomer, was prepared as follows. To a solution of cis-4-(4-bromo-phenoxy)-L-proline methyl ester (0.2 g) (0.66 mmol) (Preparation 4) and $K_2CO_3$ (0.09 g) (1 eq.) in 10 mL of DMF at 0° C. was added 3,5-dichlorophenyl isocyanate (0.12 g) (1 eq.). The reaction mixture was allowed to warm to 20° C. and was stirred overnight. After adding water, the mixture was extracted with EtOAc. The combined organic extracts were washed with water, dried over $MgSO_4$, and evaporated under reduced pressure to afford after $SiO_2$ chromatography (eluent: DCM), the above-titled compound (60 mg). Mp=116° C. NMR (DMSO, 200 MHz): 7.75 (1H, m), 7.5–7.4 (4H, d+d), 6.85 (2H, d), 5.1 (1H, m), 4.6 (1H, dd), 3.95 (1H, dd), 3.35 (1H, dd), 2.7–2.5 (1H, m), 2.25 (1H, bd).

Examples 3–9

Compounds having the formula (II), above, wherein m, $R_{11}$, and W have the values listed in Table 4 and the bonds depicted as wavy bonds define the isomers identified in Table 4, were produced using the same or similar method as for Example 2, starting with an appropriate methyl ester.

TABLE 4

| Example No. | $R_{11}$ | W | m | Stereo-Isomer | Mp (° C.) | NMR ($CDCl_3$, 200 MHz) |
|---|---|---|---|---|---|---|
| 3 | H | O | 1 | 7aR, 6R | 82 | 7.4–7.05(8H,m), 4.5–4.2(4H,m+dd), 4.1(1H,m),3.05(1H,dd), 2.45–2.15(2H,m) |
| 4 | 4-Br | S | 1 | 7aS,6S | 136 | 7.45(2H,d), 7.35(3H,m), 7.2(2H,d), 4.32(1H,dd), 4.0–4.1(1H,m), 3.70 (2H,s), 3.25–3.4(2H,m), 2.45–2.65(1H,m), 2.0–2.15(1H,m) |

TABLE 4-continued

| Example No. | $R_{11}$ | W | m | Stereo-Isomer | Mp (° C.) | NMR (CDCl$_3$, 200 MHz) |
|---|---|---|---|---|---|---|
| 5 | 4-Br | O | 1 | 7aS, 6S | 134 | 7.4(2H,d), 7.35(1H,m), 7.0–7.15(4H,m), 4.25–4.50(4H,m), 4.15 (1H,m), 3.05(1H,dd), 2.25–2.55(2H,m) |
| 6 | 4-Br | O | 1 | 7aR, 6R | 135 | 7.4(2H,d), 7.35(1H,m), 7.0–7.15(4H,m), 4.25–4.50(4H,m), 4.15 (1H,m), 3.05(1H,dd), 2.25–2.55(2H,m) |
| 7 | 4-CN | O | 1 | 7aS, 6S | 210 | 7.56(2H,d), 7.34(1H,m), 7.30(2H,d), 7.06(2H,d), 4.55–4.30(4H,dd+m), 4.20(1H,m), 3.10(1H,dd), 2.52–2.28(2H,m) |
| 8 | 3-Br | O | 1 | 7aS, 6S | Nd | 7.5–7.35(3H,m), 7.2–7.1 (4H,m), 4.5–4.25(4H,m), 4.2–4.1(1H,m), 3.06 (1H,dd), 2.55–2.25(2H,m) |
| 9 | 4-(2-CN Ph) | O | 1 | 7aS, 6S | Nd | 7.75(1H,d), 7.77.6(1H,m), 7.55–7.4(4H,m), 7.4–7.2 (6H,m), 4.56(1H,d), 4.45–4.3(3H,m), 4.25–4.15 (1H,m), 3.1(1H,dd), 2.55–2.25(2H,m) |

Example 10

(7aS,6S)-2-(3,5-dichloro-phenyl)-6-(6-isoquinolinyl methoxy)-tetrahydro-pyrrolo[1,2-c]imidazole-1,3-dione

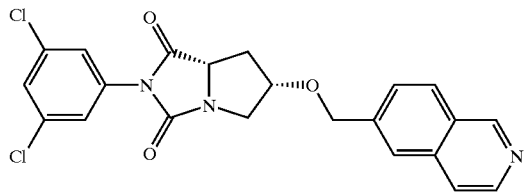

Using the same procedure as in Example 2, (7aS,6S)-2-(3,5-dichloro-phenyl)-6-(6-isoquinolinyl methoxy)-tetrahydro-pyrrolo[1,2-c]imidazole-1,3-dione was obtained starting with the appropriate methyl ester. Mp=144° C., NMR (CDCl$_3$, 200 MHz) 8.9 (1H, dd), 7.95–8.05 (2H, m), 7.65–7.5 (2H, m), 7.37 (1H, dd), 7.22 (1H, m), 7.08 (2H, m), 4.65 (1H, d), 4.53 (1H, d), 4.45–4.3 (2H, m), 4.25 (1H, m), 3.1 (1H, dd), 2.6–2.25 (2H, m).

Example 11

5-[2-(4-Chlorophenyl)ethyl]-2-(3,5-dichlorophenyl) tetrahydropyrrolo[3,4-c]pyrrole-1,3(2H,3aH)-dione

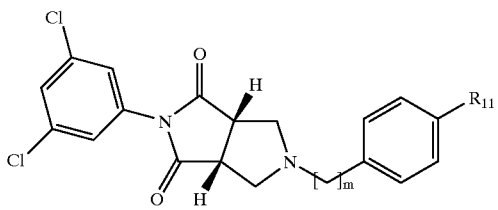

(Im)

To prepare the compound of formula (Im), wherein $R_{11}$ is chloro and m is 2, TFA (32 µl, 0.41 mmol) was added to an ice-cooled mixture of 4-chloro-N-(methoxymethyl)-N-[(trimethylsilyl)methyl]benzeneethanamine (1.5 g, 5.25 mmol) (Preparation 14) and N-(3,5-dichlorophenyl)succinimide (1 g, 4.13 mmol, prepared according to Fujinami et al., *Agr. Biol. Chem.* [1972], p. 318, incorporated herein by reference) in methylene chloride (10 mL). The reaction mixture was allowed to warm to RT over 3 h. The solution was washed with ammonium hydroxide. The organic layer was dried over MgSO$_4$ and concentrated in vacuo to afford after chromatography over silica gel (CH$_2$Cl$_2$) the above-referenced compound as a white solid (1.56 g). Mp=115° C. $^1$H NMR (CDCl$_3$): 7.40 (1H, br s), 7.15–7.35 (4H, m), 7.07 (2H, d, J=8.3 Hz), 3.4–3.5 (2H, m), 3.3–3.4 (2H, m), 2.55–2.8 (4H, m), 2.35–2.5 (2H, m).

Examples 12–14

Compounds having the formula (Im), above, wherein m is 1 and $R_{11}$ has the values listed in Table 5 were produced using the same or similar method as for Example 11, starting with an appropriately-substituted N-(methoxymethyl)-N-[(trimethylsilyl)methyl]benzenemethanamine.

TABLE 5

| Example No. | $R_{11}$ | $^1$H NMR (CDCl$_3$) | Mp (° C.) |
|---|---|---|---|
| 12 | H | 7.40 (1H,m), 7.2–7.35 (7H,m), 3.63 (2H,s), 3.39 (2H,d,J=9.9 Hz), 3.2–3.35 (2H,m), 2.4–2.55 (2H,m). | 145 |
| 13 | OMe | 7.41 (1H,br s), 7.27 (2H,br s), 7.14 (2H,d,J=8.4 Hz), 6.85 (2H,d,J=8.4 Hz), 3.80 (3H,s), 3.57 (2H,s), 3.25–3.45 (4H,m), 2.46 (2H,br t). | 82 |
| 14 | Br | 7.35–7.55 (3H,m), 7.27 (2H,br s), 7.10 (2H,d,J=8.3 Hz), 3.57 (2H,s), 3.25–3.5 (4H,m), 2.35–2.55 (2H,m). | 152 |

Example 15

7-[2-(4-Bromophenyl)ethyl]-2-(3,5-dichlorophenyl)-tetrahydro-imidazo[1,5-a]pyrazine-1,3-dione

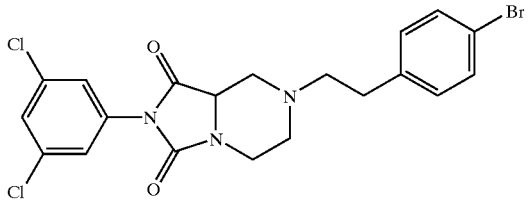

A mixture of 1-bromo-4-(2-bromoethyl)benzene (101 mg, 0.38 mmol, prepared as described in *Synth.Commun* [1996], 26, pp. 1467–1472), 2-(3,5-dichlorophenyl)-tetrahydro-imidazo[1,5-a]pyrazine-1,3-dione (100 mg, 0.33 mmol, Prep. 19), potassium carbonate (48 mg, 0.35 mmol) and sodium iodide (10 mg, 0.06 mmol) in methyl isopropyl ketone (2 mL) was heated at 100° C. for 48 h. The precipitate was discarded and the filtrate was concentrated under vacuum and chromatographed over silica gel ($CH_2Cl_2$). The obtained oil was treated with $Et_2O/HCl$ to yield the hydrochloride of 7-[2-(4-bromophenyl)ethyl]-2-(3,5-dichlorophenyl)-tetrahydro-imidazo[1,5-a]pyrazine-1,3-dione as a white solid (60 mg). $^1H$ NMR ($CDCl_3$) of the free base: 7.25–7.4 (5H, m), 7.00 (2H, d, J=8.3Hz), 4–4.15 (2H, m), 3.32 (1H, dd, $J_1$=4.1 Hz, $J_2$=11.1 Hz), 3.09 (1H, dt), 2.87 (1H, br d), 2.5–2.8 (4H, m), 1.95–2.15 (2H, m)

Example 16

7-[2-(4-Bromophenyl)-1-methyl-2-oxo-ethyl]-2-(3,5-dichlorophenyl)-tetrahydro-imidazo[1,5-a]pyrazine-1,3-dione

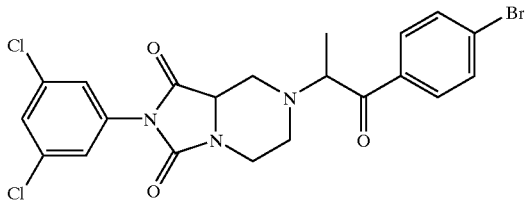

Using the same procedure as in Example 15, 7-[2-(4-bromophenyl)-1-methyl-2-oxo-ethyl]-2-(3,5-dichlorophenyl)-tetrahydro-imidazo[1,5-a]pyrazine-1,3-dione was obtained. $^1H$ NMR ($CDCl_3$): 7.85–8.0 (2H, m), 7.62 (2H, d), 7.3–7.5 (3H, m), 4–4.4 (3H, m), 3.4–3.55 (1H, m), 2.9–3.3 (2H, m), 2.6–2.8 (1H, m), 2.3–2.5 (1H, m), 1.25–1.4 (3H, m). Hydrochloride: Mp=230–235° C.

Example 17

(7aS,6S)-4-{[2-(3,5-dichloro-phenyl)-1,3-dioxo-hexahydro-pyrrolo[1,2-c]imidazol-6-ylamino]-methyl}-benzonitrile

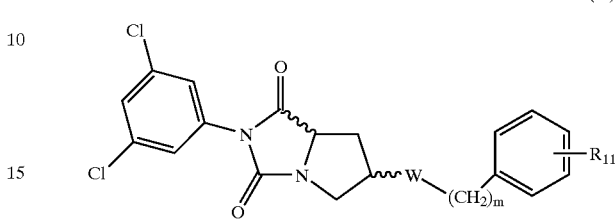

(In)

The compound of formula (In), wherein $R_{11}$ is 4-cyano, m is 1, W=NH, and the bonds depicted as wavy bonds define the 7aS,6S stereoisomer, was prepared as follows. To a solution of (7aS)-2-(3,5-dichloro-phenyl)-tetrahydro-pyrrolo[1,2-c]imidazole-1,3,6-trione (0.5 g) (0.0017 mol) (Preparation 20), in 50 mL of DCM was added molecular sieves 4A, 4-cyanobenzyl amine (0.27 g) (0.002 mol), then $NaBH(OAc)_3$ (0.54 g) (0.00255 mol.). The reaction mixture was stirred overnight at RT and then the insoluble material eliminated. After evaporating the solvent, the residue was purified by $SiO_2$ chromatography (eluent: DCM/MeOH 98/2) to afford the titled compound and its stereoisomer. 7aS,6S stereoisomer (70 mg). NMR (CDCl3, 200 MHz): 7.45 (2H, d), 7.3 (1H, m), 7.2–7.1(4H, m), 4.25 (1H, dd), 4.05 (1H, d), 3.65 (2H, dd), 3.4(1H, m), 3.02 (1H, dd), 2.35–2.2 (1H, m), 2.0 (1H, bd).

Examples 18–22

Compounds having the formula (In), above, wherein m, $R_{11}$, and W have the values listed in Table 6 and the bonds depicted as wavy bonds define the isomers identified in Table 6, were produced using the same or similar method as for Example 17, starting with an appropriate amine.

TABLE 6

| Example No. | $R_{11}$ | W | m | Stereo-Isomer | NMR (CDCl$_3$, 200 MHz) |
|---|---|---|---|---|---|
| 18 | 4-Br | NMe | 1 | 7aS, 6S | 7.41–7.34(5H,m), 7.08(2H,d), 4.31(1H,dd), 4.05(1H,d), 3.45 (2H,s), 3.35–3.15(2H,m), 2.43–2.05(2H,m), 2.1(3H,s) |
| 19 | 4-Br | NH | 2 | 7aS, 6S | 7.40–7.35(5H,m), 7.0(2H,d), 4.25(1H,dd), 4.0(1H,d), 3.35 (1H,m), 3.05(1H,dd), 2.85–2.5 (4H,m), 2.35–2.2(1H,m), 2.0(1H,bd). |
| 20 | 4-Br | NH | 3 | 7aS, 6S | 7.45–7.35(5H,m), 6.97(2H,d), 4.28(1H,dd), 3.95(1H,d), 3.35 (1H,m), 3.05(1H,dd), 2.65–2.45(4H,m), 2.35–2.2(1H,m), 2.0(1H,bd), 1.75–1.55(2H,m). |
| 21 | 4-CN | NEt | 1 | 7aS, 6S | 7.55(2H,d), 7.4–7.3(5H,m), 4.3(1H,t), 3.9(1H,dd), 3.7–3.55 (4H,s+m), 3.37(1H,dd),2.65–2.5(2H,m), 2.45–2.3(1H,m), 2.15–2.0(1H,m), 1.0(3H,t) |

TABLE 6-continued

| Example No. | $R_{11}$ | W | m | Stereo-Isomer | NMR (CDCl$_3$, 200 MHz) |
|---|---|---|---|---|---|
| 22 | 4-CN | NPr | 1 | 7aS, 6S | 7.55(2H,d), 7.45–7.3(5H,m), 4.25(1H,t), 3.85–3.6 (4H,s+m), 3.4(1H,dd), 2.5–2.3 (2H,m), 2.05–1.9(1H,m), 2.15–2.0(1H,m), 1.5–1.3(2H,m), 0.8(3H,t) |

Example 23

(7aS,6S)-N-(4-cyano-benzyl)-N-[2-(3,5-dichloro-phenyl)-1,3-dioxo-hexahydro-pyrrolo[1,2-c]imidazol-6-yl]-acetamide

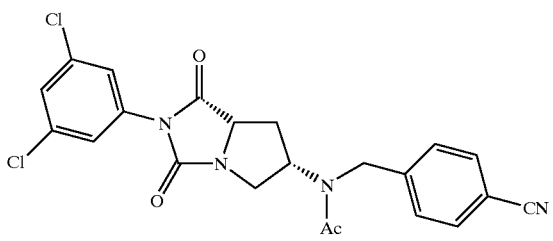

To a solution of (7aS,6S)-4-{[2-(3,5-dichloro-phenyl)-1,3-dioxo-hexahydro-pyrrolo[1,2-c]imidazol-6-ylamino]-methyl}-benzonitrile (13 mg) (0.0313 mmol) (Ex. 17) in 0.5 mL of DCM was added 10 μl (2.2 eq.) of TEA, then 6 μl of acetyl chloride (2eq.) at RT and the mixture stirred 1 h. The organic layer was washed with water, dried over MgSO$_4$, and evaporated in vacuo to afford the above-titled compound as an oily residue (6 mg). NMR (CDCl$_3$, 200 MHz): 7.69 (2H, d), 7.45 (2H, m), 7.35 (1H, m), 7.29 (2H, d), 4.57 (2H, s), 4.35–4.2 (2H, m), 3.9 (1H, dd), 3.45 (1H, dd), 2.5–2.3 (2H, m), 2.1 (3H, s)

Example 24

(6R,7aS)-[6-(4-bromobenzyloxy)-2-(3,5-dichlorophenyl)-1,3-dioxo-tetrahydro-pyrrolo[1,2-c]imidazol-7a-yl]-acetic acid methyl ester

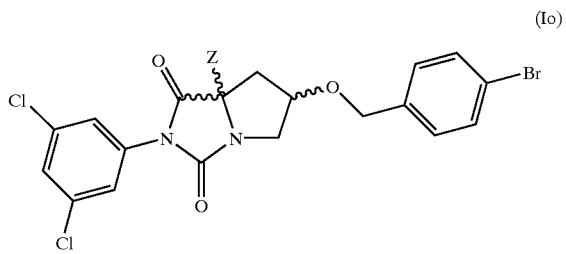

(Io)

The compound of formula (Io), wherein Z is methoxycarbonylmethyl and the bonds depicted as wavy bonds define the 7aS,6R stereoisomer, was prepared as follows. 1.65 mL of a solution of LDA (1 M) in THF (1.5 eq.) was added to a solution of (7aR,6R)-2-(3,5-dichloro-phenyl)-6-(4-bromobenzyloxy)-tetrahydro-pyrrolo[1,2-c]imidazole-1,3-dione (500 mg) (1.1 mmol) (Ex. 6) in 5 mL of dry THF cooled to −65° C. under nitrogen. The reaction mixture was stirred for 1 h then treated with a solution of methyl bromoacetate (340 mg) (2 eq.) in 3 mL of THF. After 1 h at −65° C., the reaction mixture was allowed to warm to −20° C., stirred for 2 h, and then poured in a mixture of water/EtOAc (1:1, 20 mL). The organic layer was washed with water, dried over MgSO$_4$, and evaporated under reduced pressure. The resulting oily residue was purified over SiO$_2$ column (25 g) (eluent: EtOAc/cyclohexane 3/7) to afford the above-titled compound (28.8 mg) as a foam. NMR (CDCl$_3$, 200 MHz): 7.43 (2H, d), 7.35 (1H, m), 7.15–7.0 (4H, m), 4.4–4.2 (3H, dd+m), 4.15 (1H, m), 3.7 (3H, s), 3.2–3.0 (2H, dd+d), 2.75 (1H, d), 2.52 (1H, dd), 2.05 (1H, dd).

Examples 25–26

Compounds having the formula (Io), above, wherein Z has the values listed in Table 7 and the bonds depicted as wavy bonds define the isomers identified in Table 7 were produced using the same or similar method as for Example 24 starting with an appropriate alkylating agent.

TABLE 7

| Example No. | Z | Stereo-Isomer | $^1$H NMR (CDCl$_3$) |
|---|---|---|---|
| 25 | Me | 7aR, 6R | 7.4 (2H,d), 7.33 (1H,m), 7.15–7.05 (4H,d+d), 4.45–4.2 (3H,dd+m), 4.15 (1H,m), 3.1 (1H,dd), 2.55 (1H,dd), 1.93 (1H,dd), 1.55 (3H,s) |
| 26 | CH$_2$OH | 7aR, 6S | 7.45 (2H,d), 7.35 (2H,m), 7.15 (2H,d), 7.05 (1H,m), 6.95 (OH), 4.65–4.5 (2H,m), 4.35 (1H,d), 4.25 (1H,m), 3.75–3.55 (2H, m), 2.9–2.7 (1H,m), 2.3–2.1 (1H,m) |

Examples 27

5-[2-(4-Bromophenyl)-2-oxoethyl]-2-(3,5-dichlorophenyl)-tetrahydropyrrolo[3,4-c]pyrrole-1,3-dione

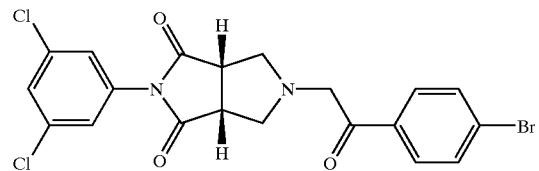

To a suspension of 2-(3,5-dichlorophenyl)-tetrahydropyrrolo[3,4-c]pyrrole-1,3(2H,3aH)-dione hydrochloride (100 mg, 0.31 mmol) (Preparation 17) in DCM (2 mL) was added TEA (150 μl), followed by 2-4'-dibromoacetophenone (95 mg, 0.34 mmol) in DCM (2 mL). After 24 h at RT, the solvent was removed and the residue chromatographed over silica gel (eluent: DCM/acetone 95/5). The resulting oil was crystallized in ether to yield the above compound as a white solid (38 mg), Mp=150° C.

Example 28

2-(3,5-Dichlorophenyl)-5-naphthalen-2-ylmethyl-tetrahydropyrrolo[3,4-c]pyrrole-1,3-dione

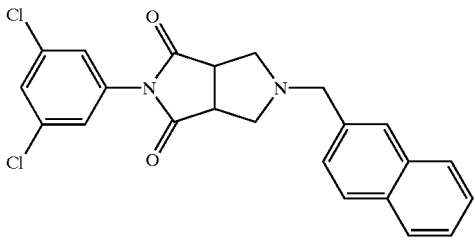

NaBH(OAc)₃ (25.4 mg, 0.12 mmol) in DCM (1 mL) was added to a solution of Preparation 17 (17.1 mg, 0.06 mmol) and 2-naphthaldehyde (14 mg, 0.09 mmol) in DCM (0.4 mL). After 24 h at RT, the product was purified over an SCX cartridge to yield Example 29 above (20.5 mg). LC Mass: retention time 2.58 min, MW: 466 (M+41, M+CH₃CN).

Example 29

(7aS,6S)-2-(3,5-dichloro-phenyl)-6-(4-bromobenzoyloxy)-tetrahydro-pyrrolo[1,2-c]imidazole-1,3-dione

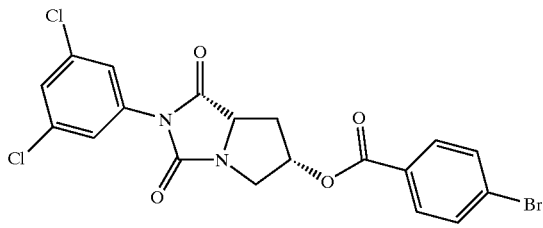

To a solution of (7aS,6S)-2-(3,5-dichloro-phenyl)-6-hydroxy-tetrahydro-pyrrolo[1,2-c]imidazole-1,3-dione (0.6 g) (0.002 mol) (Preparation 3) and TEA (0.2 mL) (0.002 mol) in 10 mL of DCM at 0° C. was slowly added 4-bromobenzoyl chloride (0.44 g) (0.09 mol) in 5 mL of DCM. The temperature was allowed to warm to 20° C., and the mixture was stirred overnight. The organic layer was washed with water, NaHCO₃ solution, water, dried over MgSO₄, and evaporated in vacuo to afford after SiO₂ chromatography (eluent: DCM/Pet. Ether—50/50) the above-titled compound as a white solid (0.24 g). NMR (CDCl₃, 200 MHz): 7.68 (2H, d), 7.50 (2H, d), 7.38 (1H, m), 7.25 (2H, d), 5.55 (1H, m), 4.46 (1H, dd), 4.36 (1H, d), 3.38 (1H, dd), 2.65–2.59 (2H, m).

Example 30

10a-(4-Bromo-benzyl)-2-(3,5-dichloro-phenyl)-10,10a-dihydro-5H-imidazo[1,5-b]isoquinoline-1,3-dione

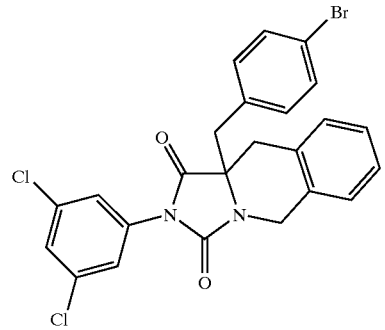

To a solution of (S)-2-(3,5-dichloro-phenyl)-10,10a-dihydro-5H-imidazo[1,5-b]isoquinoline-1,3-dione (100 mg) (0.1 mmol) (Prep. 22) in 2.5 mL of dry THF at −40° C. was added a 1 M solution of LIHMDS (0.5 mL) in THF. The reaction mixture was stirred for 15 min. at −40° C. and a solution of 4-bromobenzyl bromide (70 mg) in 1 mL of dry THF was added. The reaction mixture was stirred at −50 C. for 30 min., allowed to warm to RT, stirred overnight, then partitioned between brine and t-Bu methyl ether. The organic layer was dried over MgSO₄, concentrated in vacuo, and the residue purified by HPLC to afford the above compound (34.5 mg). NMR (CDCl₃, 200 MHz): 7.45 (2H, d), 7.25–7.35 (5H, m), 6.95–7.0 (4H, d+d), 5.15 (1H, d), 4.55 (1H, d), 3.25 (2H, s), 3.20 (1H, d), 2.95 (1H, d).

We claim:

1. A compound having the formula (I),

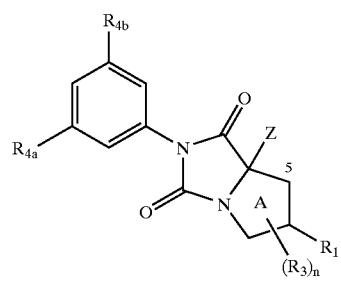

(I)

or a pharmaceutically-acceptable salt thereof, in which:

Z is hydrogen, alkyl, or substituted alkyl, except Z is not arylalkyl or heteroarylalkyl;

R₁ is Q-aryl or Q-heteroaryl, wherein Q is —W—(CH₂)ₘ—;

W is selected from —O—, —NR₁₀—, —S—;

R₃ is attached to any available carbon atom of ring A and at each occurrence is selected independently of each other R₃ from halogen, alkyl, substituted alkyl, alkenyl, nitro, cyano, OR₈, NR₈R₉, CO₂R₈, (C=O)R₈, C(=O)NR₈R₉, NR₈C(=O)R₉, NR₈C(=O)OR₉, OC(=O)R₈, OC(=O)NR₈R₉, SR₈, S(O)qR₈ₐ, NR₈SO₂R₉, SO₂NR₈R₉, aryl, heteroaryl, heterocyclo, cycloalkyl, and keto (=O), provided that when R₃ is attached to the atom designated as the C-5 atom of ring A, then R₃ is not aryl or heteroaryl;

R₄ₐ and R₄ᵦ are selected independently of each other from the group consisting of hydrogen, halogen, alkyl, substituted alkyl, alkenyl, nitro, cyano, hydroxy, alkoxy, substituted alkoxy, phenyloxy, benzyloxy, CO$_2$H, C(=O)H, amino, alkylamino, substituted alkylamino, CO$_2$alkyl, (C=O)alkyl, and alkylthio;

R$_8$ and R$_9$ (i) selected independently of each other are hydrogen, alkyl, substituted alkyl, alkenyl, alkynyl, alkoxy, cycoalkyl, aryl, heteroaryl, or heterocyclo; or (ii) taken together form a heterocyclo ring;

R$_{8a}$ is alkyl, substituted alkyl, cycloalkyl, aryl, heteroaryl, or heterocyclo;

R$_{10}$ is hydrogen, alkyl, or substituted alkyl;

n is 0, 1, or 2;

q is 1, 2, or 3; and m is 0, 1, 2, 3, or 4.

2. The compound of claim 1, or a pharmaceutically-acceptable salt thereof, wherein:

Z is hydrogen, lower alkyl, or lower alkyl substituted with hydroxy, alkoxy, halogen, cyano, nitro, amino, or alkylamino;

R$_3$ is attached to any available carbon atom of ring A other that T and is selected from halogen, alkyl, substituted alkyl, alkenyl, cyano, OR$_8$, NR$_8$R$_9$, CO$_2$R$_8$, (C=O)R$_8$, C(=O)NR$_8$R$_9$, NR$_8$C(=O)R$_9$, NR$_8$C(=O)OR$_9$, SR$_8$, S(O)$_4$R$_{8a}$, NR$_8$SO$_2$R$_9$, SO$_2$NR$_8$R$_9$, and keto (=O);

R$_{4a}$ and R$_{4b}$ are selected independently of each other from the group consisting of hydrogen, halogen, alkyl, alkoxy, cyano, nitro, haloalkyl, haloalkoxy;

R$_8$ and R$_9$ are selected independently of each other are hydrogen or alkyl, and R$_{8a}$ is alkyl; and m is 0, 1, or 2; and n is 0 or 1.

3. The compound of claim 1, or a pharmaceutically-acceptable salt thereof, wherein:

W is —O—, —NR$_{10}$—, or —S—, wherein R$_0$ is hydrogen, lower alkyl, or lower alkyl substituted with CO$_2$H or CO$_2$alkyl; and m is 0, 1, or 2.

4. A compound according to claim 3 having the formula:

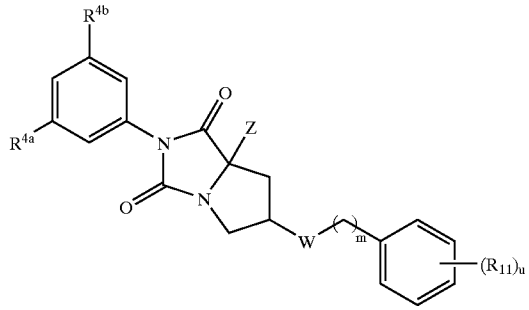

or a pharmaceutically-acceptable salt thereof, wherein R$_{11}$ is selected from halogen, C$_{1-4}$alkyl, nitro, cyano, hydroxy, C$_{1-4}$alkoxy, haloalkyl, haloalkoxy, CO$_2$H, C(=O)H, amino, C$_{1-4}$alkylamino, CO$_2$C$_{1-4}$alkyl, (C=O)C$_{1-4}$alkyl, C$_{1-4}$alkylthio, phenyl, phenyloxy, benzyl, and benzyloxy, and u is 0, 1, or 2.

5. A compound according to claim 1, having the formula,

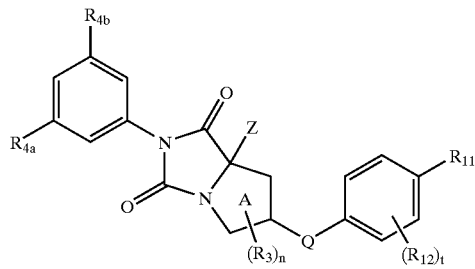

or a pharmaceutically-acceptable salt thereof, wherein:

Z is hydrogen, alkyl, or alkyl substituted with hydroxy, alkoxy, halogen cyano, nitro, amino, or alkylamino;

R$_{11}$ is hydrogen, halogen, alkyl, alkoxy, haloalkyl, haloalkoxy, nitro, or cyano;

R$_3$ and R$_{12}$ are independently selected from alkyl, substituted alkyl, halogen, haloalkyl, haloalkyloxy, nitro, cyano, hydroxy, alkoxy, amino, alkylamino, acyl, alkoxycarbonyl, carbamyl, sulfonyl, and sulfonamide;

n is 0 or 1; and t is 0, 1, or 2.

6. A compound according to claim 5, or a pharmaceutically-acceptable salt thereof, in which R$_{4a}$ and R$_{4b}$ are both halogen.

7. A compound having the formula (Ia),

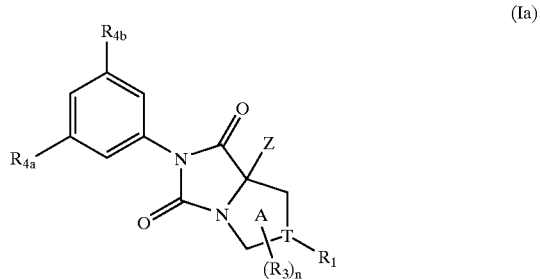

(Ia)

or a pharmaceutically-acceptable salt thereof, in which:

Z is hydrogen, alkyl, alkyl substituted with hydroxy, halogen, cyano, amino, alkylamino; or when R$_1$ together with an R$_3$ group join to form a benzo ring fused to ring A, Z is arylalkyl or heteroarylalkyl;

R$_1$ is (a) —W—(CH$_2$)$_m$—Ar, or (b) taken together with an R$_3$ group to form a benzo ring fused to ring A, in which case Z is arylalkyl or heteroarylalkyl;

Ar is aryl or heteroaryl substituted with zero or one R$_{11}$ and zero to two R$_{12}$ groups;

T is CR$_5$;

W is selected from —O—, —NR$_{10}$—, and —S—;

R$_3$ is selected independently of each other R$_3$ from halogen, alkyl, substituted alkyl, alkenyl, nitro, cyano, keto (=O), OR$_8$, NR$_8$R$_9$, CO$_2$R$_8$, (C=O)R$_8$, C(=O) NR$_8$R$_9$, NR$_8$C(=O)R$_9$, NR$_8$C(=O)OR$_9$, OC(=O)R$_8$, OC(=O)NR$_8$R$_9$, SR$_8$, S(O)$_q$R$_{8a}$, NR$_8$SO$_2$R$_9$, SO$_2$NR$_8$R$_9$, aryl, heteroaryl, heterocyclo, and cycloalkyl; and/or one R$_3$ together with R$_1$ may join to form a fused benzo ring;

R$_5$ is hydrogen, halogen, alkyl, alkenyl, hydroxy, nitro, cyano, hydroxy alkoxy, amino, or alkylamino, or C$_{1-4}$ alkyl optionally substituted with hydroxy, amino, alkylamino, halogen, or cyano;

$R_{4a}$ and $R_{4b}$ are selected independently of each other from the group consisting of hydrogen, halogen, alkyl, nitro, cyano, haloalkyl, and haloalkoxy;

$R_8$ and $R_9$ (i) selected independently of each other are hydrogen, alkyl, substituted alkyl, cycloalkyl, aryl, heteroaryl, or heterocyclo; or (ii) taken together form a heterocyclo ring;

$R_{8a}$ is alkyl, substituted alkyl, cycloalkyl, aryl, heteroaryl, or heterocyclo;

$R_{11}$ is hydrogen, halogen, alkyl, hydroxy, alkoxy, amino, alkylamino, haloalkyl, haloalkoxy, nitro, or cyano;

$R_{12}$ is alkyl, substituted alkyl, halogen, haloalkyl, haloalkoxy, nitro, cyano, hydroxy, alkoxy, substituted alkoxy, amino, alkylamino, acyl, alkoxycarbonyl, carbamyl, sulfonyl, sulfonamide;

$R_{10}$ and $R_{13}$ are independently hydrogen, alkyl, or substituted alkyl;

m is 0, 1, 2, 3, or 4;

n is 0, 1 or 2; and q is 1, 2, or 3.

8. A compound according to claim 7, having the formula:

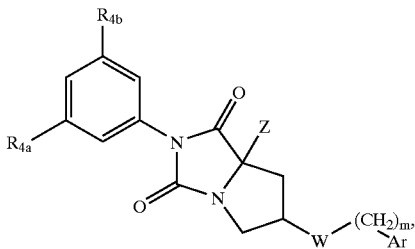

or a pharmaceutically-acceptable salt thereof, wherein Ar is phenyl or isoquinolinyl and Ar is substituted with zero or one $R_{11}$ and zero $R_{12}$ groups.

9. A compound according to claim 8 having the formula,

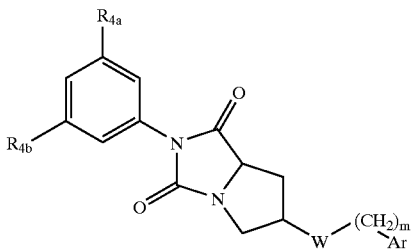

in which
the groups W—$(CH_2)_m$—Ar taken together are selected from:

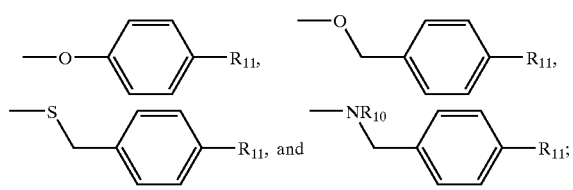

$R_{10}$ is selected from hydrogen, lower alkyl, and lower alkyl substituted with $CO_2H$ or $CO_2$alkyl, and $R_{11}$ is selected from hydrogen, bromo, chloro, cyano, methoxy.

10. A compound according to claim 9, or a pharmaceutically-acceptable salt thereof, in which $R_{4a}$ and $R_{4b}$ are both chloro.

11. A compound according to claim 9, in which the groups W—$(CH_2)_m$—Ar taken together are selected from:

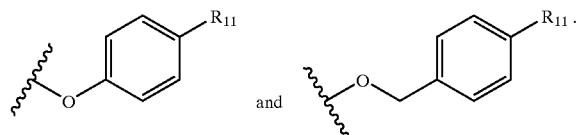

12. A compound according to claim 11, or a pharmaceutically-acceptable salt thereof, in which $R_{4a}$ and $R_{4b}$ are both chloro and $R_{11}$ is chloro, bromo, or cyano.

13. A compound according to claim 1 which is: (I)

(7aS,6S)-2-(3,5-dichloro-phenyl)-6-(4-bromophenoxy)-tetrahydro-pyrrolo[1,2-c]imidazole-1,3-dione;

(7aS,6S)-2-(3,5-dichloro-phenyl)-6-(4-bromophenoxy)-tetrahydro-pyrrolo[1,2-c]imidazole-1,3-dione;

(7aS,6S)-2-(3,5-dichloro-phenyl)-6-(4-bromobenzyloxy)-tetrahydro-pyrrolo[1,2-c]imidazole-1,3-dione;

(7aR,6R)-2-(3,5-dichloro-phenyl)-6-(4-bromobenzyloxy)-tetrahydro-pyrrolo[1,2-c]imidazole-1,3-dione;

(7aS,6S)-2-(3,5-dichloro-phenyl)-6-(4-cyanobenzyloxy)-tetrahydro-pyrrolo[1,2-c]imidazole-1,3-dione;

(7aS,6S)-2-(3,5-dichloro-phenyl)-6-benzyloxy-tetrahydro-pyrrolo[1,2-c]imidazole-1,3-dione;

(7aS,6S)-2-(3,5-dichloro-phenyl)-6-(3-bromobenzyloxy)-tetrahydro-pyrrolo[1,2-c]imidazole-1,3-dione;

(7aS,6S)-2-(3,5-dichloro-phenyl)-6-(4-[2-cyanophenyl]benzyloxy)-tetrahydro-pyrrolo[1,2-c]imidazole-1,3-dione;

(7aS,6S)-4-[[2-(3,5-dichloro-phenyl)-1,3-dioxo-hexahydro-pyrrolo[1,2-c]imidazol-6-ylamino]-methyl]-benzonitrile;

(7aS,6S)—N—(4-cyano-benzyl)-N-[2-(3,5-dichloro-phenyl)-1,3-dioxo-hexahydro-pyrrolo[1,2-c]imidazol-6-yl]-acetamide; or (6R,7aS)-[6-(4-bromobenzyloxy-2-(3,5-dichlorophenyl)-1,3-dioxo-tetrahydro-pyrrolo[1,2c]imidazol-7a-yl] acetic acid methyl ester;

(ii) a pharmaceutically-acceptable salt thereof.

14. A pharmaceutical composition for treating an inflammatory or immune disease comprising (a) at least one compound according to claim 1, or pharmaceutically acceptable salt thereof, and (b) a pharmaceutically acceptable carrier or diluent.

15. A pharmaceutical composition for treating an inflammatory or immune disease comprising (a) at least one compound according to claim 7, or a pharmaceutically acceptable salt thereof, and (b) a pharmaceutically acceptable carrier or diluent.

16. A pharmaceutical composition comprising (i) at least one compound of claim 1 or a pharmaceutically acceptable-salt thereof; (ii) one or more second compositions effective for treating an inflammatory or immune disease; and (iii) a pharmaceutically-acceptable carrier.

17. A method of treating an inflammatory or immune disease comprising administering to a mammal in need of such treatment a therapeutically-effective amount of a composition according to claim 14.

18. The method of claim 17 in which the inflammatory or immune disease is selected from rheumatoid arthritis, chronic obstructive pulmonary disease, psoriasis, and transplant rejection.

19. A method of treating a Leukointegrin/CAM-associated disease which comprises administering to a patient in need thereof an effective amount of a compound of claim 1.

* * * * *